(12) United States Patent
Donars et al.

(10) Patent No.: US 8,352,007 B2
(45) Date of Patent: Jan. 8, 2013

(54) OXIMETER DEVICE

(75) Inventors: Dave Donars, New Berlin, WI (US); Robert Rammel, Muskego, WI (US); Matthew L. Brown, Waukesha, WI (US); Guy A. Smith, Waukesha, WI (US)

(73) Assignee: Smiths Medical ASD, Inc., Rockland, MA (US)

( * ) Notice: Subject to any disclaimer, the term of this patent is extended or adjusted under 35 U.S.C. 154(b) by 1092 days.

(21) Appl. No.: 12/292,093

(22) Filed: Nov. 12, 2008

(65) Prior Publication Data
US 2010/0121164 A1    May 13, 2010

(51) Int. Cl.
    *A61B 5/00*       (2006.01)
    *B65D 85/38*     (2006.01)
    *B65D 69/00*     (2006.01)
    *B65D 71/00*     (2006.01)
    *B65D 57/00*     (2006.01)
    *B65D 25/04*     (2006.01)
    *B65D 1/36*      (2006.01)
    *B65D 1/24*      (2006.01)

(52) U.S. Cl. ........ 600/323; 600/310; 600/344; 206/305; 206/569; 206/570; 220/528

(58) Field of Classification Search .................. 600/310, 600/322, 323, 344; 206/305, 306, 363, 569, 206/570; 220/23.9, 52.8; 422/401–403
See application file for complete search history.

(56) References Cited

U.S. PATENT DOCUMENTS

| | | | |
|---|---|---|---|
| 5,839,439 A | 11/1998 | Nierlich et al. | |
| 5,944,659 A | 8/1999 | Flach et al. | |
| 6,575,904 B2 * | 6/2003 | Nagai et al. | 600/301 |
| 7,057,889 B2 * | 6/2006 | Mata et al. | 600/301 |
| 7,156,807 B2 | 1/2007 | Carter et al. | |
| 2002/0069885 A1 | 6/2002 | Boies et al. | |
| 2003/0181798 A1 | 9/2003 | Al-Ali | |
| 2005/0122469 A1 | 6/2005 | Martel | |
| 2005/0197550 A1 | 9/2005 | Al-Ali et al. | |
| 2006/0007882 A1 | 1/2006 | Zeng et al. | |
| 2006/0056363 A1 | 3/2006 | Ratiu et al. | |
| 2006/0142808 A1 * | 6/2006 | Pearce et al. | 607/5 |
| 2006/0276714 A1 | 12/2006 | Holt et al. | |
| 2007/0030116 A1 | 2/2007 | Feher | |
| 2007/0135866 A1 | 6/2007 | Baker et al. | |
| 2007/0180140 A1 | 8/2007 | Welch et al. | |
| 2007/0255250 A1 | 11/2007 | Moberg et al. | |
| 2007/0258395 A1 | 11/2007 | Jollota et al. | |
| 2007/0262863 A1 | 11/2007 | Aritsuka et al. | |
| 2008/0004538 A1 | 1/2008 | Virtanen | |
| 2008/0108884 A1 * | 5/2008 | Kiani | 600/301 |
| 2008/0221420 A1 | 9/2008 | Grubac et al. | |
| 2008/0272918 A1 | 11/2008 | Ingersoll | |

* cited by examiner

*Primary Examiner* — Jeffrey G Hoekstra
*Assistant Examiner* — Megan Leedy
(74) *Attorney, Agent, or Firm* — Louis Woo

(57) ABSTRACT

An oximeter has a housing configured to have a cavity defining portion that is adapted to be fitted with covers of various dimensions to effect receptacles of different dimensions for accommodating differently sized sensor of sensor assemblies that are matable to the oximeter for sensing physical attributes of a patient. Each of the covers, once fully fitted to the housing, is fixedly latched thereto unless a force that overcomes the latching is applied to remove the cover. The effected receptacle is adapted to biasedly retain a corresponding sensor placed therein. The holstered sensor therefore would not accidentally fall out or be removed from the receptacle, until the user deliberately applies a force to remove the sensor from the receptacle.

20 Claims, 27 Drawing Sheets

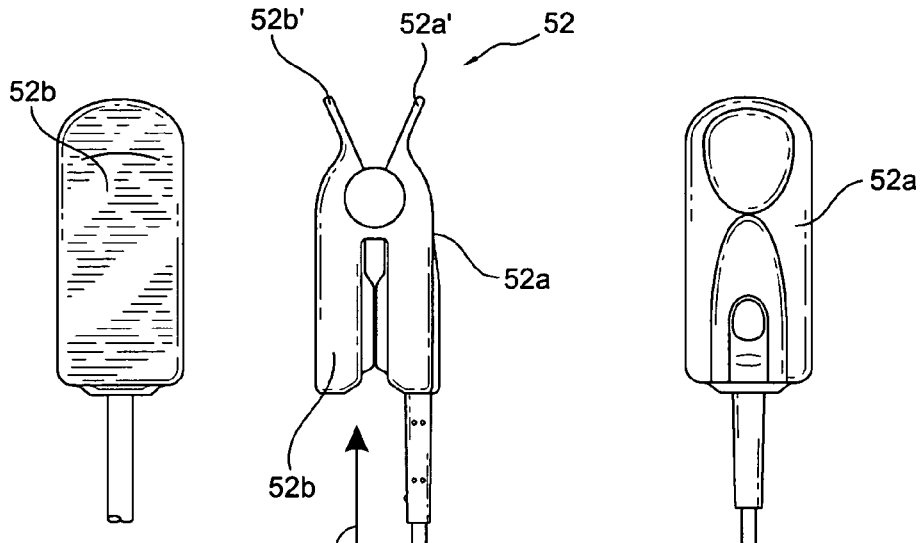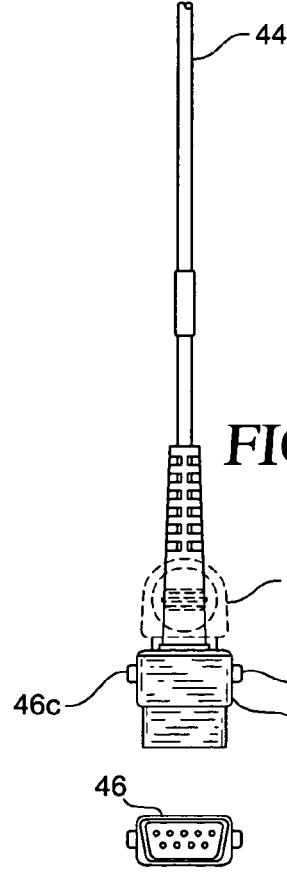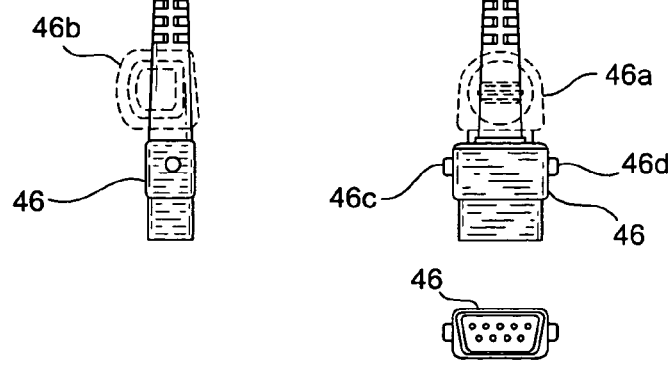
FIG. 6c
FIG. 6a
FIG. 6b
FIG. 6d

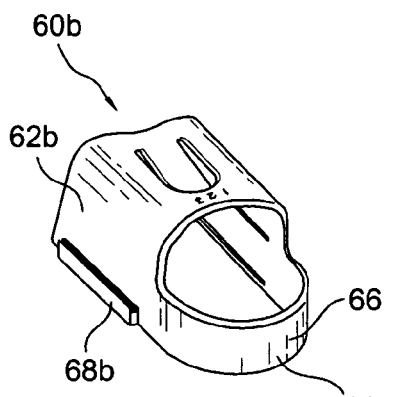
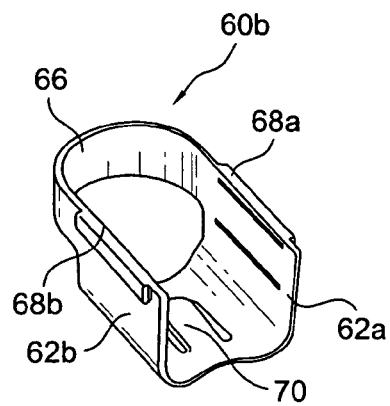
FIG. 11a   FIG. 11b
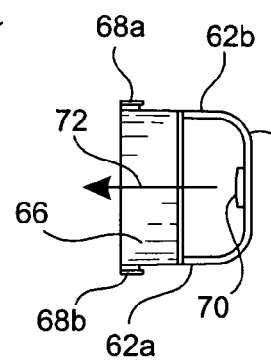
FIG. 11f
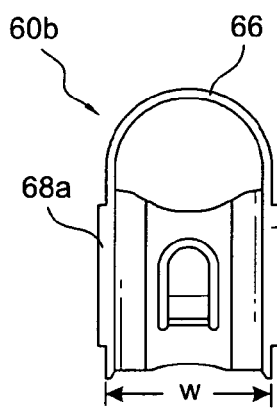 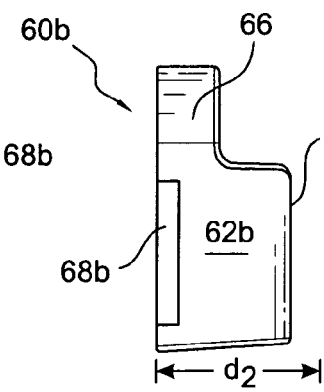 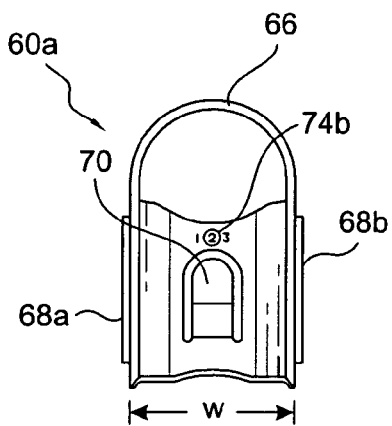
FIG. 11d   FIG. 11c   FIG. 11e
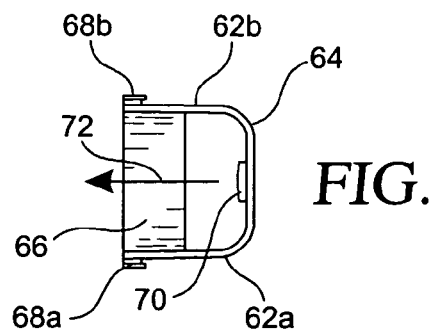
FIG. 11g

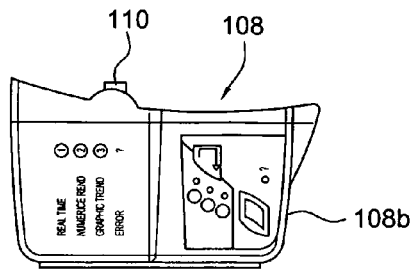
FIG. 24c
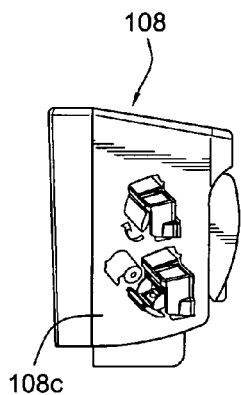
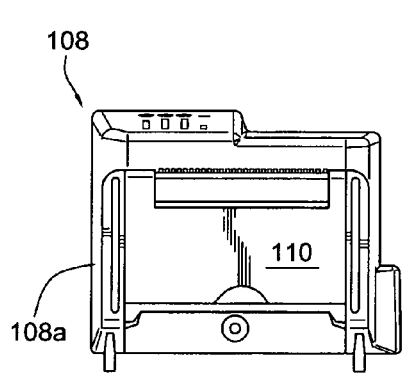
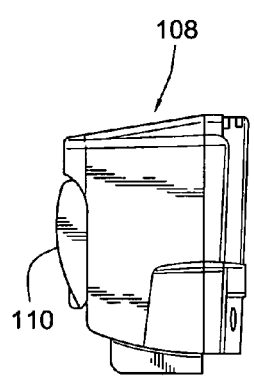
FIG. 24d  FIG. 24a  FIG. 24e
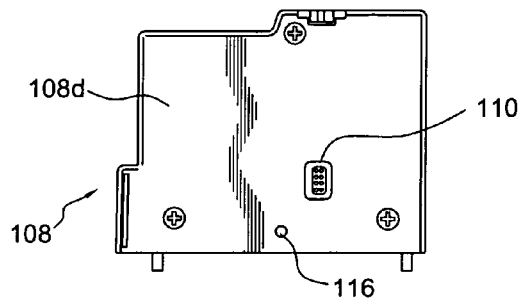
FIG. 24b

OXIMETER DEVICE

CROSS REFERENCE TO RELATED APPLICATIONS

This application is related to U.S. patent application Ser. No. 12/285,663 filed Oct. 10, 2008, entitled "Wireless Telecommunications System Adaptable for Patient Monitoring" and is also related to U.S. design application Ser. No. 29/309,835, filed Oct. 23, 2008, entitled "Oximeter Device", both applications having been assigned to the same assignee as the instant invention.

FIELD OF THE INVENTION

The present invention relates to oximeters and more particularly to a new oximeter device that has a housing that is reconfigurable to have receptacles of different sizes for retaining sensors of different dimensions.

BACKGROUND OF THE INVENTION

There are different types of handheld oximeter devices currently on the market. Some of those are oximeters that are fitted to a digit of a patient. An example of one such oximeter is the DIGIT being sold by the assignee of the instant invention. Another type of the oximeter devices is a handheld device that has connected thereto, by means of a cable, a sensor that is used to measure the physical parameters or attributes, for example the blood saturation oxygen level ($SpO_2$), of the patient by having the patient insert one of his fingers into the sensor. Examples of such handheld oximeter units include those sold by the assignee of the instant invention under product Nos. 3301, 3303 and 3403, among others. There are also compact monitors to which a sensor may be connected by means of a cable to measure the physical attributes of a patient. An example of this is the AutoCorr digital pulse oximeter sold by the assignee of the instant invention under product No. 3304. For the above noted oximeter devices that are available in the market, after use, the sensor would simply be placed along side of the oximeter device, as there are no compartments in those devices for stowing the sensor. So, too, since an oximeter is often used with differently dimensioned sensors, for example an adult sensor and a pediatric sensor, the need arises not only for a storage space to store the sensor, but also that the storage space be able to securely store sensors of different sizes, so that a small sensor would not readily fall out of the storage space design to hold a large sensor.

SUMMARY OF THE PRESENT INVENTION

The oximeter device of the instant invention has a newly designed housing that has a cavity defined by a back wall portion at its back and two sidewalls extending from the back wall that come together to form a base. The cavity has two longitudinal grooves, one on each side of the sidewalls. A boss or protuberance forms at the lower end of the back wall adjacent to the base. The width of the cavity, as separated by the sidewalls, is designed to accommodate any one of a multiple numbers of receptacle covers of different dimensions. Each of the covers is configured to be attached to the housing, and once attached, it further defines the cavity by effecting a receptacle of a given dimension that is adapted to hold firmly a corresponding sensor.

Each of the receptacle covers has two sidewalls that extend from a front wall. The sidewalls and the front wall of the receptacle have substantially the same longitudinal length as the sidewalls that define the cavity at the housing of the oximeter device. The two sidewalls of the cover each extend beyond the front wall downwardly to form an end insert. The insert is configured to form fit to the base that defines the cavity at the housing. Thus, if the base for the cavity is semicircular, then the end insert of the cover is rounded to form fit to the curved base. Respective flanges are provided longitudinally along each sidewall of the cover to slide along the corresponding grooves at the sidewalls that define the cavity at the housing so that the cover may be guidedly affixed to the housing of the oximeter device. Once the cover is attached to the housing, a receptacle is formed at the back of the housing—with the back wall of the housing, the cover and the two sidewalls of the cover that overlie the two sidewalls that define the cavity providing the four sides for the receptacle. The receptacle may also be referred to as a holster, storage space or pocket. When the cover is fully inserted along the sidewalls of the defined cavity, an edge of the cover end insert, which is in the form of a curved band, would coact with the protuberance at the back wall of the cavity, so that the cover is firmly affixed to the housing of the oximeter device. To remove the receptacle cover, a user has to apply a predetermined force that overcomes the latching force of the protuberance to the end insert to push the receptacle out of the cavity of the housing.

By providing a receptacle at the housing that is configurable by a plurality of differently dimensioned receptacle covers, when the oximeter device is used with different types of sensors, each of those sensors may therefore be retained or holstered in its counterpart receptacle. To ensure that the sensor is firmly retained in and not accidentally fall out of the receptacle, a prong or tongue that is formed naturally to bias inwardly to the interior of the receptacle is provided at the front wall of the receptacle cover. When the sensor that is meant to be used with the receptacle is inserted into the receptacle, the tongue at the cover would bias the sensor against the back wall of the housing to thereby firmly retain the sensor within the receptacle. The biasing force applied by the tongue of the receptacle cover is such that the sensor can readily be removed from the receptacle when the user deliberately withdraws it from the receptacle. When a sensor of a different dimension is connected to the oximeter, a correspondingly dimensioned receptacle cover is affixed to the housing of the oximeter device to configure the appropriate receptacle for that sensor.

So that a sensor may be connected to the oximeter device, a conventional connector is provided on the top of the device for mating with the connector of the sensor. As is well known, a sensor for measuring the $SpO_2$, i.e., a spectrophotometric sensor, is connected to its connector by means of a longitudinal cable. For the oximeter device of the instant invention, a senor having a coiled cable may also be connected to the device for spot checking.

The oximeter device has a second connector that allows it to dock to a docking station, so that its energy source, possibly a rechargeable battery pack, may be recharged. The connector also allows communication between the oximeter device and an external device connected to the docking station. An optional printer may be attached to the docking station for printing out the data collected and stored in the oximeter device.

The instant invention therefore relates to an apparatus comprising an housing having a screen for displaying a graphical or numerical representation of at least one sensed physical attribute of a patient. The housing has one connector adapted to mate with the a sensor connector electrically connected to a sensor attachable to the patient to senor the physical attributes of a patient. The housing further as a defined cavity portion configured to accept any one of a plurality of receptacle covers of different dimensions. The any one of these receptacle covers, once attached to the cavity portion of the housing, is removably affixed thereto until a predetermined force is applied to remove it from the cavity. The any one of the receptacle covers in combination with the defined cavity portion of the housing form a receptacle that is dimensioned to fittingly accept a corresponding sensor of a given dimension that once placed in the receptacle is securely held therein unless it is deliberately removed therefrom.

The instant invention also relates to an oximeter device that comprises a housing having a screen mounted to its front for displaying at least one graphical or numerical representation of at least one physical attribute of a patient. The housing has one connector away from the screen that is adapted to mate with a sensor connector electrically connected to a sensor attachable to the patient to sense the physical attribute of the patient. A cavity is defined at the back of the housing and the defined cavity portion of the housing is configured to accept any one of a plurality of covers of different dimensions. The any one of the covers, once attached to the cavity portion, is removably affixed thereto until a predetermined force is applied to remove it therefrom. The thus configured receptacle is dimensioned to fittingly accept a corresponding one sensor of a given dimension, the sensor being securely held in but readily removable from the configured receptacle, once it is inserted into the receptacle. A chamber is provided at the back of the housing for storing a power source for the oximeter device.

The present invention further relates to a system that comprises an oximeter device having a screen mounted to its front for displaying graphical and numerical representations of physical attributes from a patient, one connector adapted to mate with a sensor connector electrically connected to a sensor attachable to a patient to sense at least one physical attribute of the patient, a cavity portion configured to accept any one of a plurality of covers of different dimensions, the any one cover once inserted into the cavity portion is affixed thereto until a predetermined force is applied to remove it from the cavity portion, the cavity portion and the any one cover affixed thereto together form a receptacle dimensioned to fittingly accept a corresponding one sensor of a given dimension so that the corresponding one sensor is securely held in but removable from said receptacle, and an other connector; and a docking station whereonto the oximeter is docked, the other connector from the oximeter matable to a dock connector when the oximeter device is docked to said docking station.

BRIEF DESCRIPTION OF THE FIGURES

The instant invention will become apparent and will be best understood with reference to the following description of the invention taken in conjunction with the accompanying drawings, wherein:

FIG. 5a is one view of a sensor assembly having an adult finger sensor;

FIG. 5b is another view of the adult finger sensor assembly of FIG. 5a;

FIG. 5c is a plan view of the sensor head of the FIG. 5a sensor assembly;

FIG. 5d is a plan view of the connector of the FIG. 5a sensor assembly;

FIG. 6a is one view of another sensor assembly having a sensor that has a dimension that is smaller than the sensor shown in FIGS. 5a-5d;

FIG. 6b is another view of the FIG. 6a sensor assembly;

FIG. 6c is a view showing the opposite side of the sensor of the sensor assembly shown in FIG. 6b;

FIG. 6d is a plan view of the connector plug showing the pins of the connector of the FIG. 6a sensor assembly;

FIG. 8c is a plan view of the connector of the spot check sensor assembly of FIG. 8a;

FIGS. 11a and 11b are respective perspective views of a receptacle cover adapted to be affixed to the housing of an oximeter for establishing a receptacle used for accepting the sensor shown in FIGS. 6a-6d;

FIGS. 11c-11g are respective views of the side, front, back, top and bottom of the FIGS. 11a and 11b receptacle cover;

FIG. 12a and 12b are respective perspective views of the receptacle cover to be used with the pediatric or neonate sensor shown in FIG. 7a;

FIGS. 24a, 24b, 24c, 24d and 24e are respective views of the front, the back, the top, one side, and another side of a printer attachable to the docking station of FIG. 21;

DETAILED DESCRIPTION OF THE INVENTION

Figure 1:
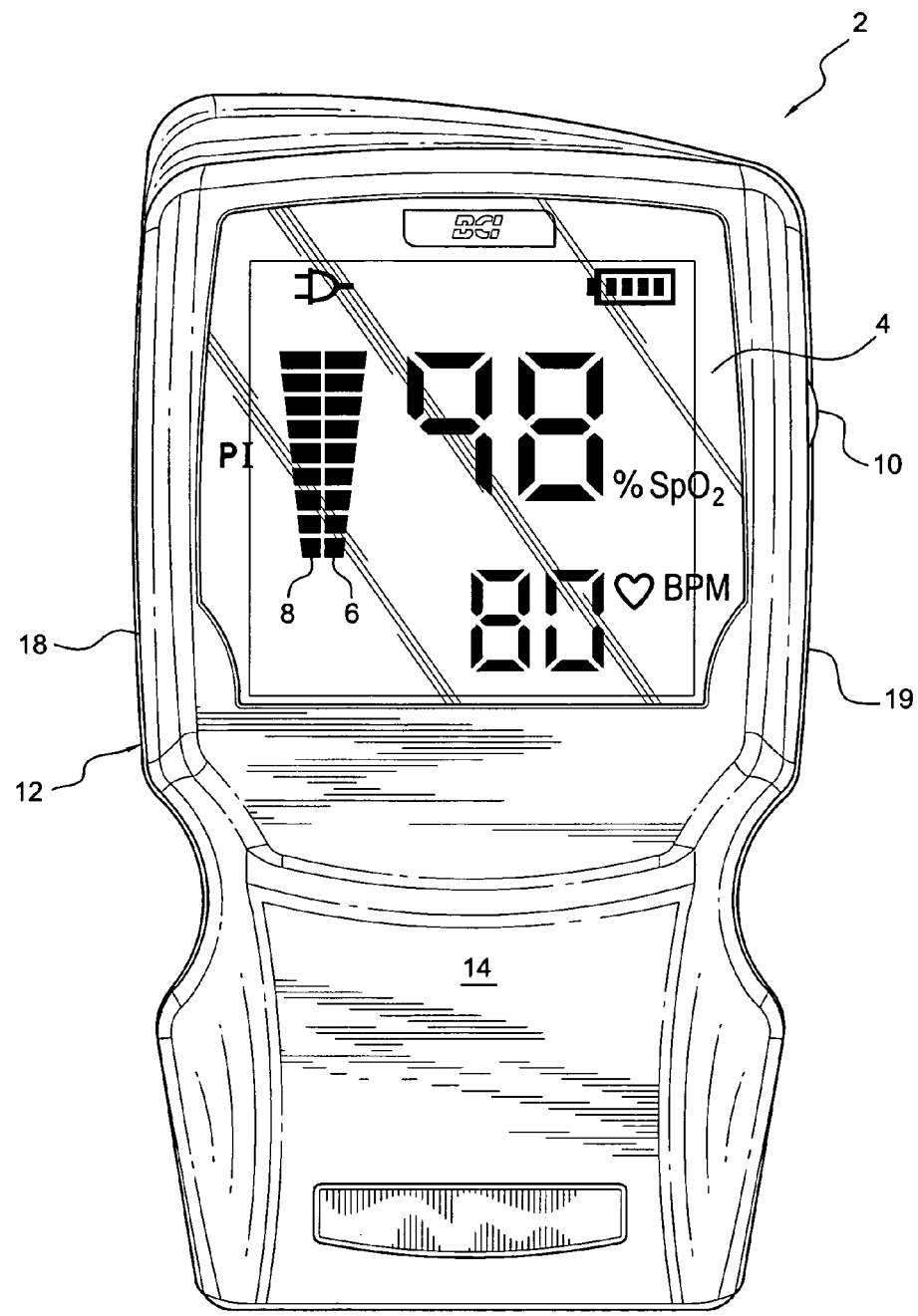
FIG. 1 is the front view of an exemplar embodiment of an oximeter of the present invention.

With reference to FIGS. 1-4, an oximeter 2 is shown. In particular, oximeter 2 is shown to have a display screen 4 for displaying graphical or numerical representations of physical attributes that are measured or sensed from a patient. In the exemplar LED display screen of FIG. 1, a number "98" represents the $SpO_2$ while the number "80" represents the pulse rate of the patient. Also shown on screen 4 is a first bar 6 of increasing widths that indicates the strength of the signal being measured, and an adjacent bar 8 that indicates the perfusion index of the patient. In most instances, the bar for the perfusion index (PI) remains relatively constant, while the bar graph 6 for the strength of the signal varies. There are other graphical representations shown on screen 4. For example, an electrical outlet is shown to indicate whether the device is connected to an AC power source, and a battery symbol provides an indication of the amount of power that remains when oximeter 2 is not connected to AC power.

The operation of the exemplar oximeter of FIGS. 1-4 may rely on the BCI Micro Power Oximeter Board, catalog No. 31392B1, or the BCI Digital Micro Power Oximeter Board, catalog No. WW3711. As these oximeter boards and the operation of an oximeter assembled with those boards are conventional, specific operations of the oximeter are deemed not to be necessary for this application. Further, the oximeter may incorporate the features disclosed in co-pending U.S. patent application Ser. Nos. 11/907,980, 11/907,981, 11/907982, 11/907,983 and 12/285,663. The respective disclosures of the just noted co-pending applications are incorporated by reference to this application. For the embodiment of the instant inventive oximeter, it is suffice to note that an on/off switch 10, when pressed, initiates the operation of the oximeter.

The housing of oximeter 2 is designated 12. Housing 12 is configured to have a front side or surface 14 per shown in FIG. 1, a back side 16 per shown in FIG. 2, a left side 18 (when viewed from the front) per shown in FIG. 3, and a left side 19 per shown in FIG. 4.

Figure 2:
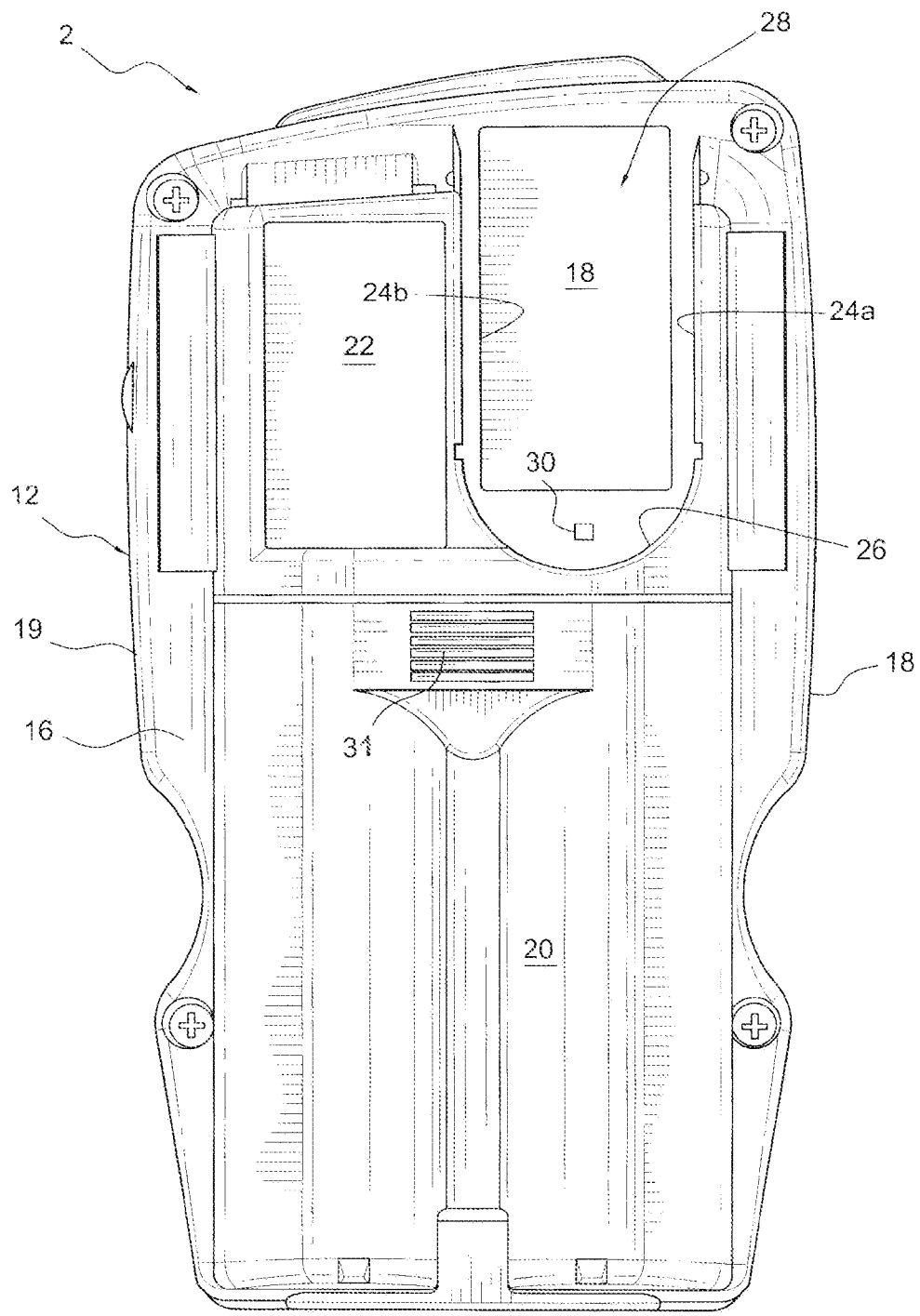
FIG. 2 is a back view of the present invention oximeter.
Figure 3:
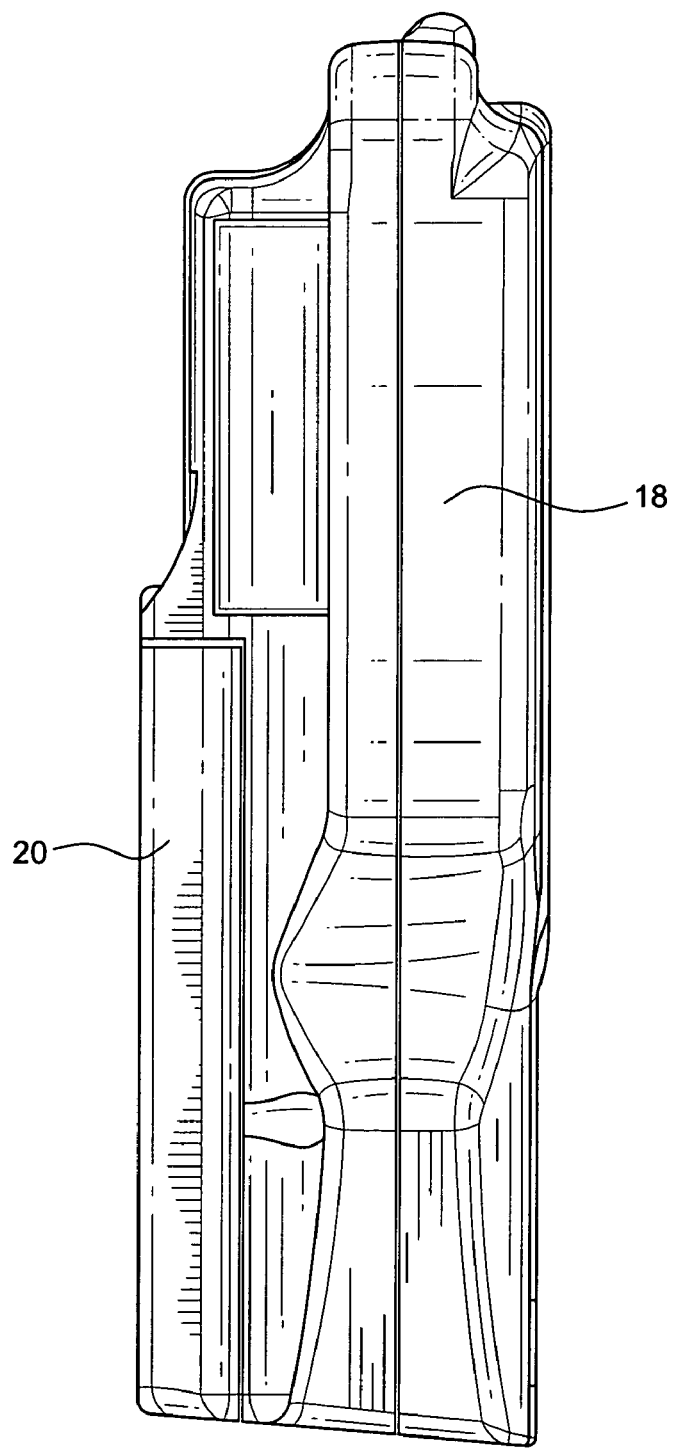
FIG. 3 is a side view of the present invention oximeter.
Figure 4:
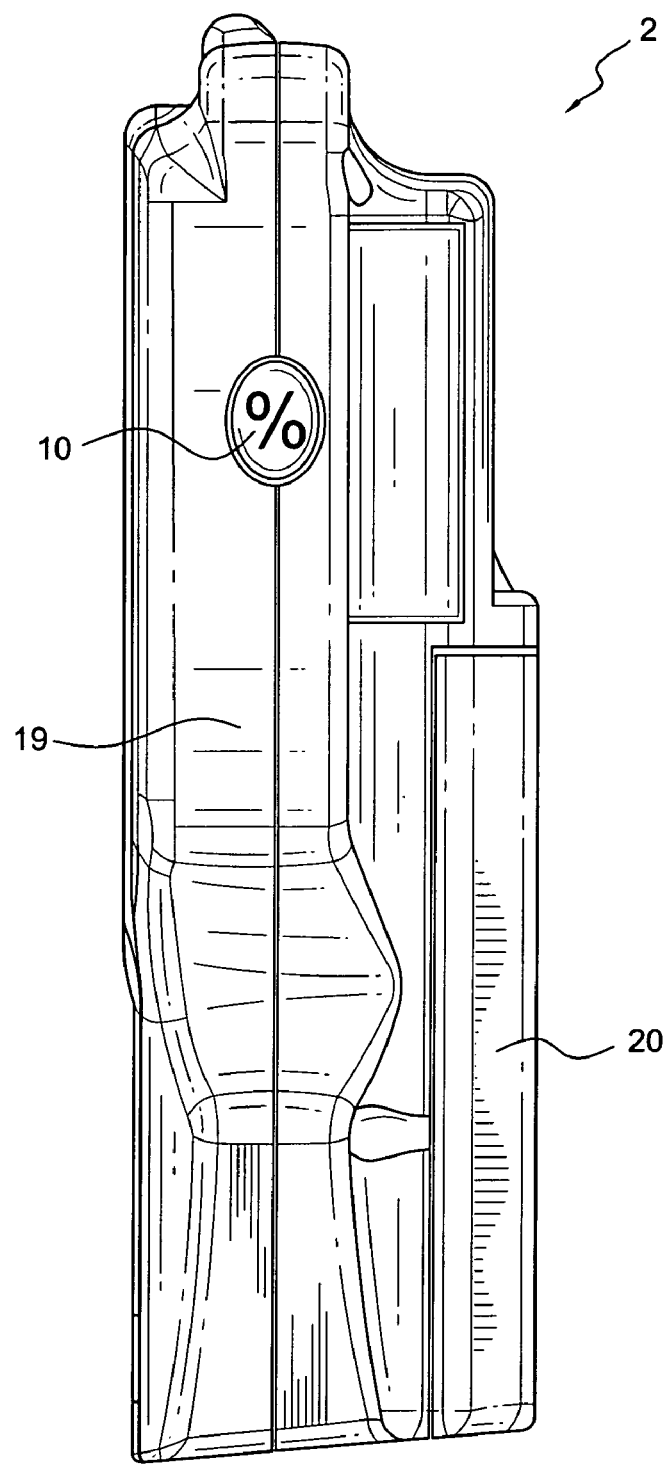
FIG. 4 is another side view of the oximeter of the present invention.

The back side 16 of oximeter 2 has a number of formations, including a back wall 18, a battery or power pack cover 20 and a raised compartment portion 22. Back wall 18 has two sidewalls 24a and 24b (see also FIG. 16) that extend from back wall 18. The sidewalls 24a and 24b extend longitudinally downwards, with respect to the oximeter housing as shown in FIG. 2, and joined to form a base 26, which is shown to be semi-circular. With back wall 18, sidewalls 24a and 24b, and base 26, a void or cavity 28 is defined at the back of housing 12. A boss or protuberance 30 is formed at the lower portion of back wall 18 adjacent to base 26. Protuberance 30 is used as a latch mechanism, to be further discussed infra.

By means of a force applied to thumb pad 31, battery cover 20 is removable from the back of housing 12. This is more clearly shown in FIG. 20 which shows a latch 32 that disengages with a catch 34 when thumb pad 31 is pressed downward, thereby enabling cover 20 to be removed from the back of housing 12 to expose a chamber 38. Further with reference to FIG. 20, a battery pack 36 that contains the power source for the oximeter, which ordinarily is fitted to chamber 38, is shown to have been removed therefrom. Further with respect to the disassembled view of FIG. 20, note that the battery pack 36 supplies power to the oximeter by way of the battery contacts 40. In place of battery pack 36, a plurality of batteries, for example four batteries as indicated by the battery outlines drawn on the back wall of chamber 38, may be used to power the oximeter.

Figures 5A, 5B, 5C, 5D:
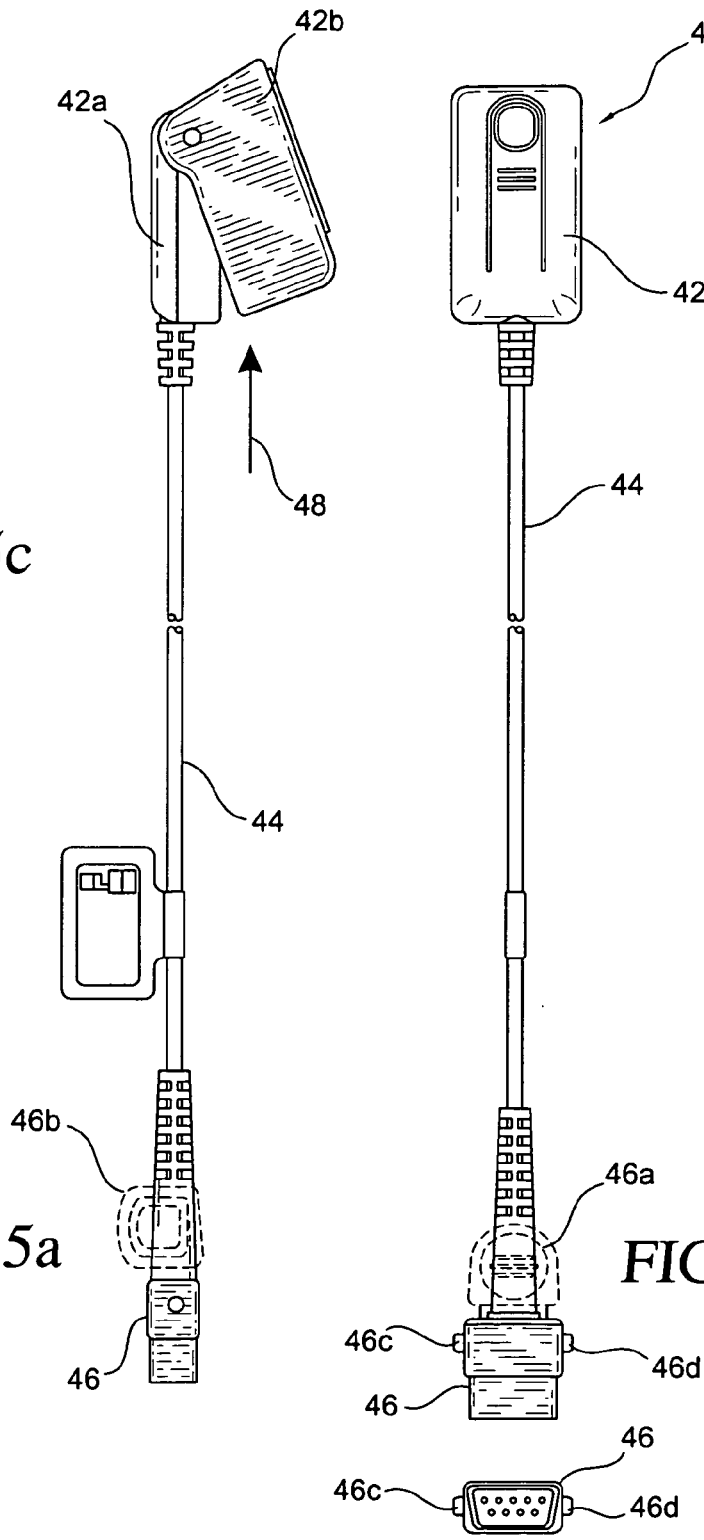

FIGS. 5a-5d, 6a-6d, 7a-7b and 8a-8c respectively illustrate the different sensor assemblies that may be used with oximeter 2 for measuring or sensing the physical attributes of a patient. The finger sensor assembly shown in FIGS. 5a-5d has a large adult size finger sensor 42 connected by a cable 44 to a connector 46. Sensor 42 has a base portion 42a and a movable portion 42b that pivots relative to base portion 42a when a patient inserts a digit, for example a finger, in the direction as indicated by directional arrow 48, for grasping the finger of the patient. Connector 46 is a conventional DB-9 connector, per clearly shown in FIG. 5d. As shown in FIG. 5b, connector 46 ordinarily has a grab tab 46a that extends longitudinally from connector 46. Grab tab 46a usually is held by the user for mating or removing connector 46 to or from the input connector 50 (FIG. 13) of oximeter 2. To facilitate the mating and removal of connector 46 to and from the input connector 50, in this instance the female connector of the oximeter, grab tab 46a may be formed at a right angle to connector 46, per shown by the dashed line grab tab 46b of FIG. 5a. The sensor 42 shown in FIGS. 5a-5d may be the adult finger sensor manufactured by the assignee of the instant invention under manufacturing No. 3044.

FIGS. 6a-6d show a second sensor assembly that has a sensor 52 having a smaller dimension than sensor 42 of FIGS. 5a-5d. Elements for the FIGS. 6a-6d sensor assembly that are the same as the FIG. 5a-5d sensor assembly are labeled the same. Sensor 52 of the FIGS. 6a-6d sensor assembly is made up of two portions 52a and 52b that are pivotable relative to each other, when their respective finger grip tabs 52a' and 52b' are pressed towards each other. Sensor 52 may be represented by the sensor manufactured by the assignee of the instant invention under manufacturing No. 3444.

Figure 7:
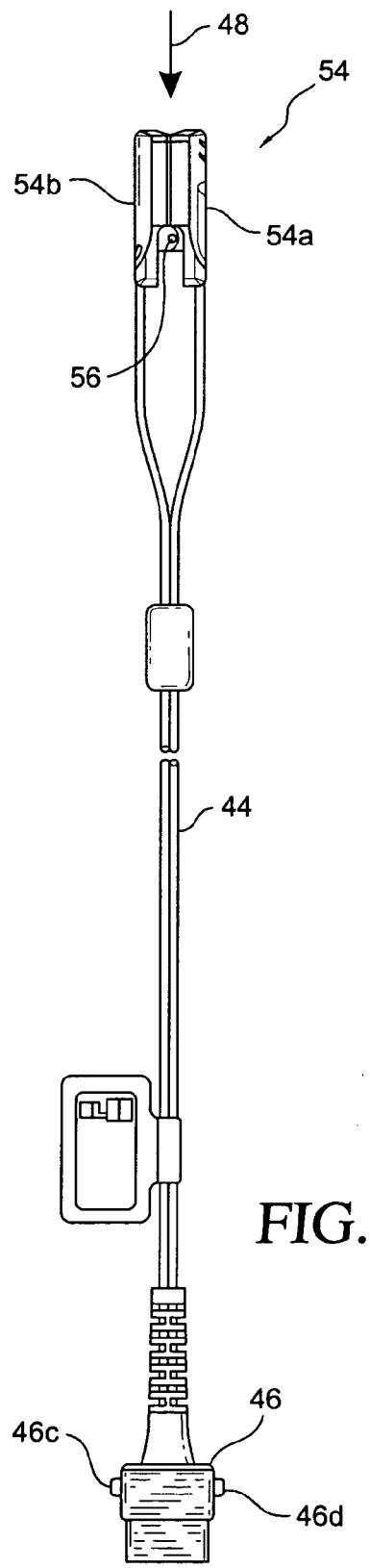
FIG. 7 shows a sensor assembly having a pediatric finger sensor that has a dimension smaller than those sensors shown in FIGS. 5a-5d and 6a-6d.

FIG. 7 illustrates a pediatric or neonate finger sensor assembly having a sensor 54 that has a dimension smaller than either of the sensors shown in FIGS. 5 and 6. Sensor 54 has two portions 54a and 54b that are pivotally connected at pivot 56 and both portions may be pivotally opened to receive a digit of a child from the direction indicated by directional arrow 48.

Figure 8A:
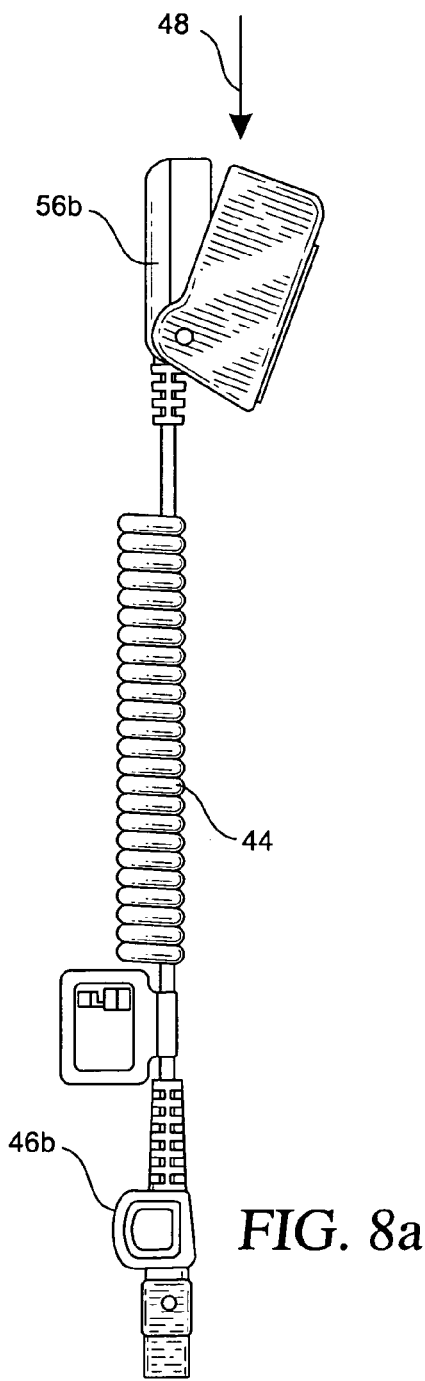
FIG. 8a is one view of a spot check sensor assembly that has a coiled cable and a grab tab at right angle to the connector.
Figure 8B:
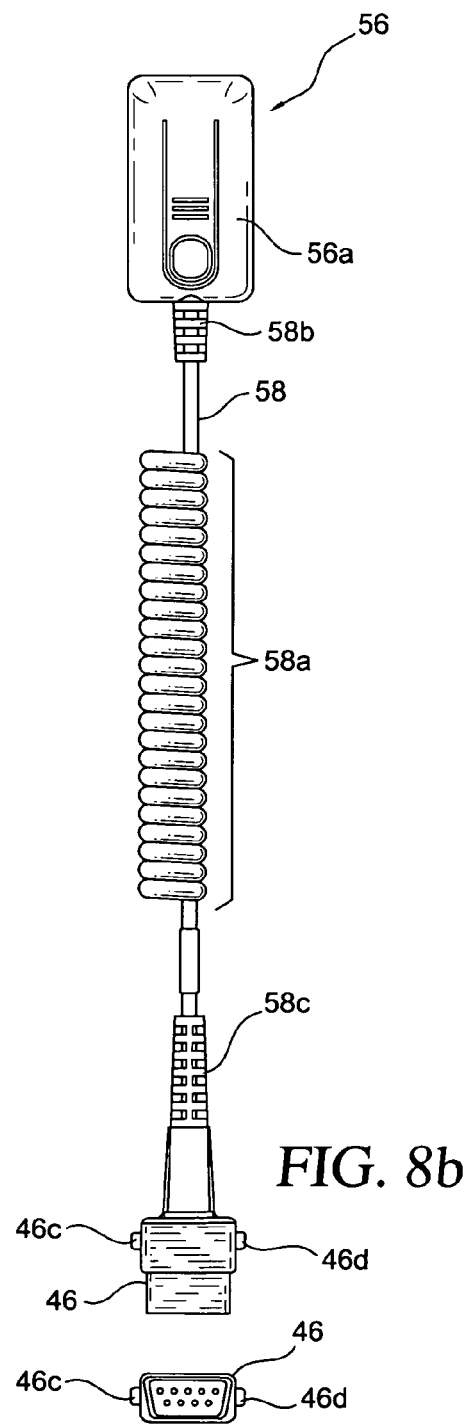
FIG. 8b is another view of the FIG. 8a sensor assembly.
Figure 8C:

FIGS. 8a-8c illustrate yet another sensor assembly that is matable to oximeter 2 for measuring the physical attributes of a patient. For the FIGS. 8a-8c sensor assembly, the sensor 56 is shown to be connected to connector 46 by a coiled cable 58. Sensor 56 is similar to sensor 42 of the FIGS. 5a-5d sensor assembly in that portion 56a is pivotable relative to base 56b. Similarly, connector 46 has its grab tab 46b at right angle to the connector per shown in FIG. 8a, to facilitate the mating and withdrawal of the male connector 46 from the input female connector 50 of oximeter 2.

As shown in FIGS. 8a and 8b, coiled cable 58 has a coiled portion 58a that is formed from a series from helical coils so that the length of cable 58 may be extended. When not in use, cable 58 is contracted to its original state per shown in FIGS. 8a and 8b. With coiled portion 58a, longitudinal tension exerted on cable 58 is absorbed. Moreover, cable 58 may not be twisted as much as a non-coiled cable such as cable 44 shown for the other sensor assemblies of FIGS. 5, 6 and 7. Tension relief sections 58b and 58c are provided at the sensor end and the connector end, respectively, of cable 58. Such tension relief portions are similarly provided for the two ends of cable 44 for the earlier discussed sensor assemblies of FIGS. 5-7. Although cable 58 has coiled portion 58a along a major portion thereof, FIGS. 8a and 8b show that cable 58 becomes straightened at both of its ends for connection to relief portions 58b and 58c. It should be appreciated however that the coiled portion 58a may in practice extend uninterrupted between tension relief sections 58b and 58c. Alternatively, coiled portion 58a may occupy a shorter length of or be interrupted multiple coiled sections along the cable 58 of the sensor assembly of FIGS. 8a-8b.

Figure 9:
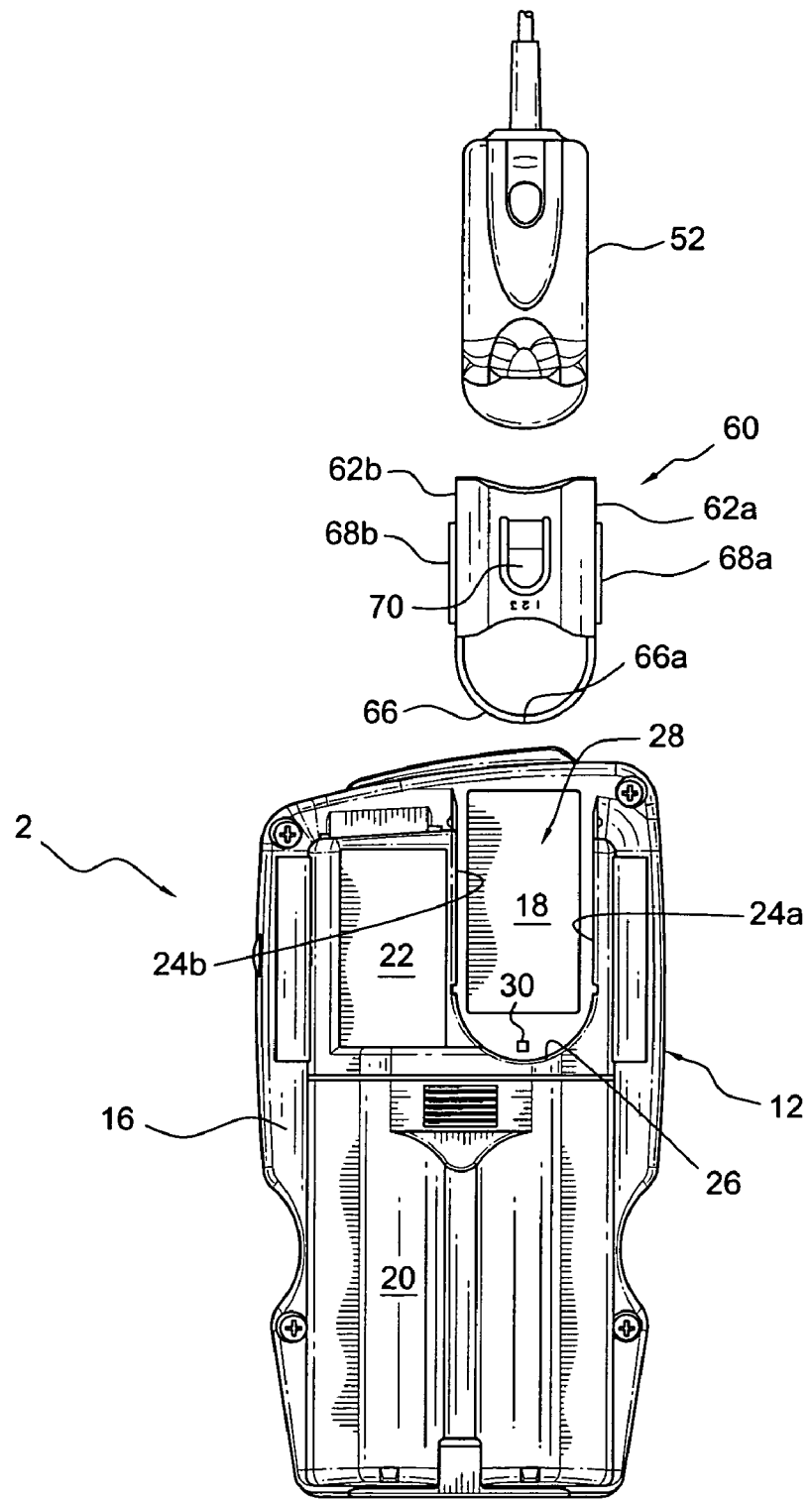
FIG. 9 illustrates the interrelationship among the oximeter device, a receptacle cover to be affixed to the housing of the device, and a sensor assembly having a corresponding sensor to be pocketed in the receptacle to be configured by the attachment of the cover to the housing.

As is with the other sensors that sense the parameters that correspond to the $SpO_2$ of a patient, sensor 56 of the sensor assembly of FIGS. 8a-8b may be referred to as a spectrophotometric sensor. As is well known, sensor 56 has at least one light emitting diode at one portion, and a photosensor at the other portion for measuring the $SpO_2$ of the patient So that the sensor of a sensor assembly is not left hanging, housing 12 of oximeter 2 has configured at its back cavity 28. As was discussed previously, cavity 28 is defined by back wall 18, sidewalls 24a and 24b, and base 26. As cavity 28 has a defined configuration and the various sensors have different dimensions, a means must be devised to enable the various dimensioned sensors to be retained at housing 12. To achieve this end, a receptacle cover, holster or clip 60 having a configured dimension is removably attached or affixed to the portion of the housing that defines cavity 28 to form a receptacle, holster or pocket of a particular dimension that is adapted to retain a correspondingly dimensioned sensor. FIG. 9 shows a receptacle cover 60 in alignment with cavity 28 and a sensor, for example sensor 52 of the sensor assembly of FIG. 6. Receptacle cover 60 is slidably fitted to cavity 28 to form a receptacle for retaining the sensor placed or deposited thereinto.

Three different receptacle cover embodiments are shown in FIGS. 10a-10g, FIGS. 11a-11g and FIGS. 12a-12g. As the distance separating sidewalls 24a and 24b that define cavity 28 is constant at the back of oximeter housing 12, to attach the receptacle cover to the cavity defining portion of housing 12, each of the receptacle covers has a width defined by its sidewalls that is slightly smaller than the distance separating sidewalls 24a and 24b. Thus, it is the depth of the receptacle, i.e., the distance between the back wall 18 of cavity 28 and the front wall of the receptacle cover that determines the dimension for the different receptacles.

Figure 10A:
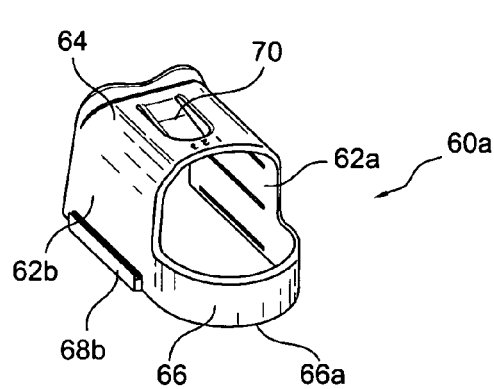
FIGS. 10a and 10b are respective perspective views of the receptacle cover that is adapted to be used with the sensor shown in FIGS. 5a-5d when affixed to the housing of the oximeter device.
Figure 10B:
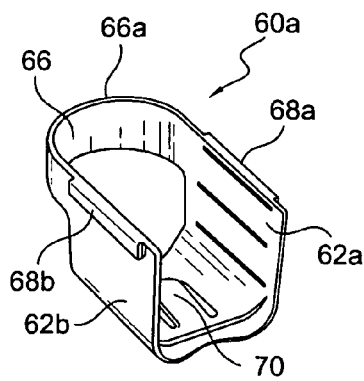
Figure 10F:
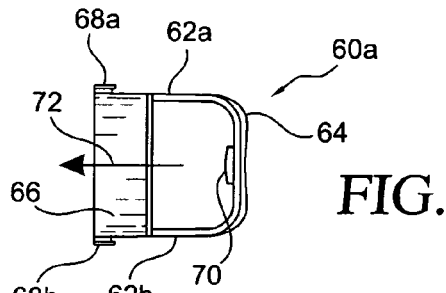
FIGS. 10c-10g are respective side, front, back, top and bottom views of the FIGS. 10a and 10b receptacle cover.
Figure 10D:
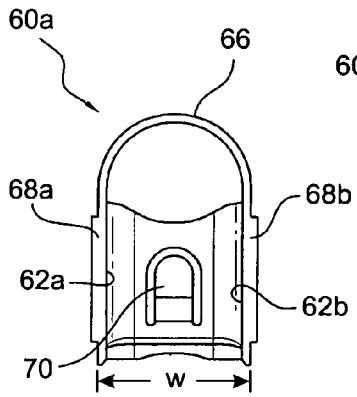
Figure 10C:
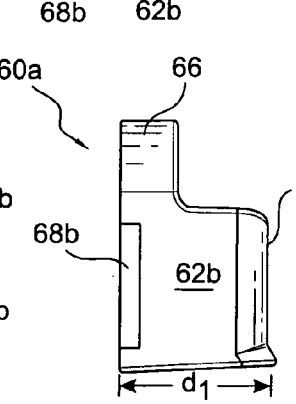
Figure 10E:
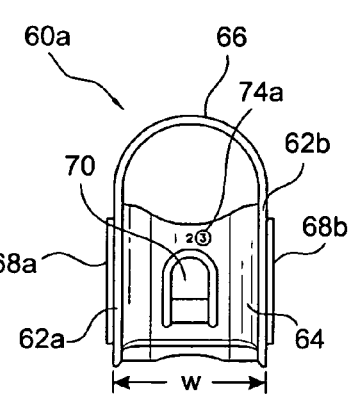

In FIGS. 10a-10g, a first receptacle cover 60a is shown to have two sidewalls 62a and 62b. These sidewalls extend from a front wall 64. The sidewalls 62a and 62b each extend longitudinally at one end to merge and form a curved end insert 66 that has one edge 66a. The respective longitudinal edges of sidewalls 62a and 62b are formed to have corresponding flanges 68a and 68b. Front wall 64 extends longitudinally only to approximately the respective ends of the sidewalls 62a and 62b that form the beginning of end insert 66, which resembles a half ring, per shown in FIGS. 10d and 10e. FIGS. 10d and 10e show the width of the receptacle cover 60a as "w". The depth of the receptacle cover 60a is designated d1, per shown in FIG. 10c.

Figure 10G:
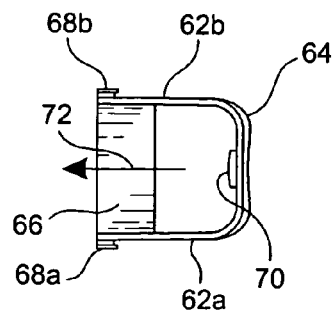

Receptacle cover 60a has at its front wall 64 a prong or tongue that biases inwardly in the direction indicated by directional arrow 72, as shown in FIGS. 10f and 10g. Also shown on the front wall 64 of receptacle 60a are three numbers, with the "3" being circled, per indicated by designation 74 in FIG. 10e. The circled number provides an indication of the size of the receptacle cover for use with a corresponding sensor. combining with cavity 23 at the housing 12 of the oximeter for accommodating that fits into the receptacle. For the exemplar embodiment of the receptacle cover 60a, the circled 3 provides an indication that the it is to be used with an adult sensor, for example the adult sensor of the sensor assembly shown in FIGS. 5a-5d.

The same components for the receptacle cover embodiments shown in FIGS. 11a-11g and FIGS. 12a-12g as those for the receptacle cover embodiment of FIGS. 10a-10g are labeled the same. As was discussed above, the major difference between the different receptacle covers is the distance from the front wall to the edge of the two sidewalls extending therefrom, i.e., the distance separating the back wall 18 of the oximeter housing 12 and the front wall 64 of the cover when the cover is affixed to the oximeter housing. For identification purposes, the receptacle cover shown in FIGS. 11a-11g is designated 60b and the distance from its front wall 64 to the respective longitudinal edges of its two sidewalls 62a and 62b is designated d2, per shown in FIG. 11c. Similarly, the designation d3 is provided to indicate the depth of the receptacle cover 60c shown in FIGS. 12a-12g. The width "w" for the three different receptacle embodiments shown in FIGS. 10, 11 and 12 remain the same, per shown in FIGS. 10e, 11e and 12e.

Figure 12A:
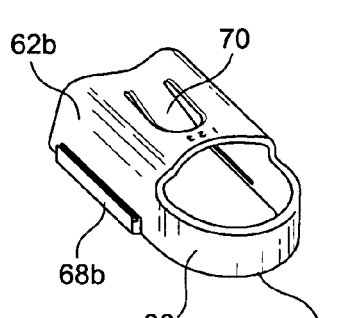
Figure 12B:
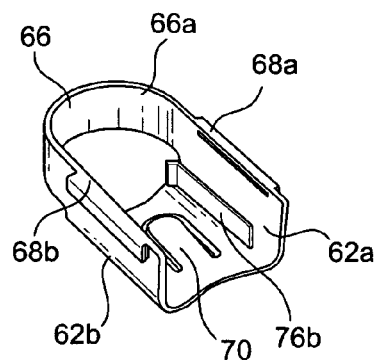
Figure 12F:
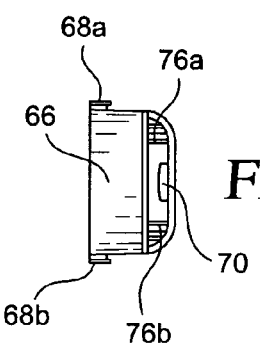
FIGS. 12c-12g are respective views of the side, front, back, top and bottom views of the receptacle cover of FIGS. 12a and 12b.
Figure 12D:
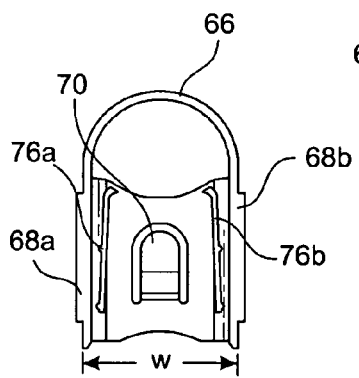
Figure 12C:
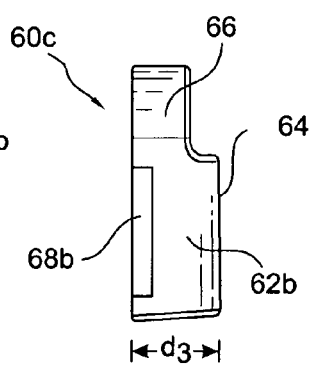
Figure 12E:
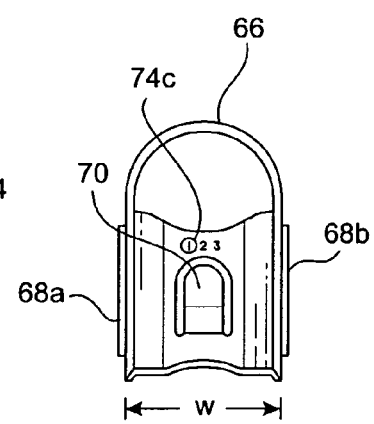
Figure 12G:
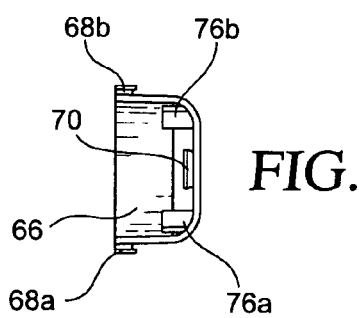

The receptacle cover shown in FIGS. 10a-10g is the largest receptacle cover and is identified as such per the number "3", designated by 74a in FIG. 10e. The receptacle cover 60b shown in FIG. 11 has a small dimension and is identified by the circled number "2", per designated 74b in FIG. 11e. The smallest of the three receptacle covers shown in FIG. 12 has the circled number "1", per designated 74c in FIG. 12e. As all of the components of the receptacle cover 60b shown in FIGS. 11a-11g are the same as those in FIGS. 10-10g, no further discussion is required. The same is true with respect to the receptacle cover 60c shown in FIGS. 12a-12g, except for the two internal alignment flanges 76a and 76b that are shown in FIG. 12d. These internal flanges are used to provide guidance for the positioning of sensor 54 for the pediatric sensor assembly as shown in FIG. 7. Sensor 54, as it is used for a child, is smaller than either of the sensors 42 and 52 of the sensor assemblies of FIGS. 5 and 6, respectively.

Thus, the receptacle cover 60a shown in FIGS. 10a-10g is used for retaining sensor 40 of the sensor assembly of FIGS. 5a-5d. The receptacle cover 60b is used to retain sensor 52 of the sensor assembly shown in FIGS. 6a-6d. And the receptacle cover 60c shown in FIGS. 12a-12e is used to retain sensor 54 of the sensor assembly shown in FIG. 7. As sensor 56 of the coiled sensor assembly of FIGS. 8a-8c has the same dimension as sensor 42 of the sensor assembly of FIGS. 5a-5d, receptacle cover 60a is used to retain sensor 56. For further discussion, to prevent ambiguities, the different receptacle covers henceforth will simply be referred to as receptacle cover 60 per shown in FIG. 9. Unless specify otherwise, the sensor for the various sensor assemblies discussed above will simply be referred to as sensor 52, per shown in FIG. 9.

Figure 13:
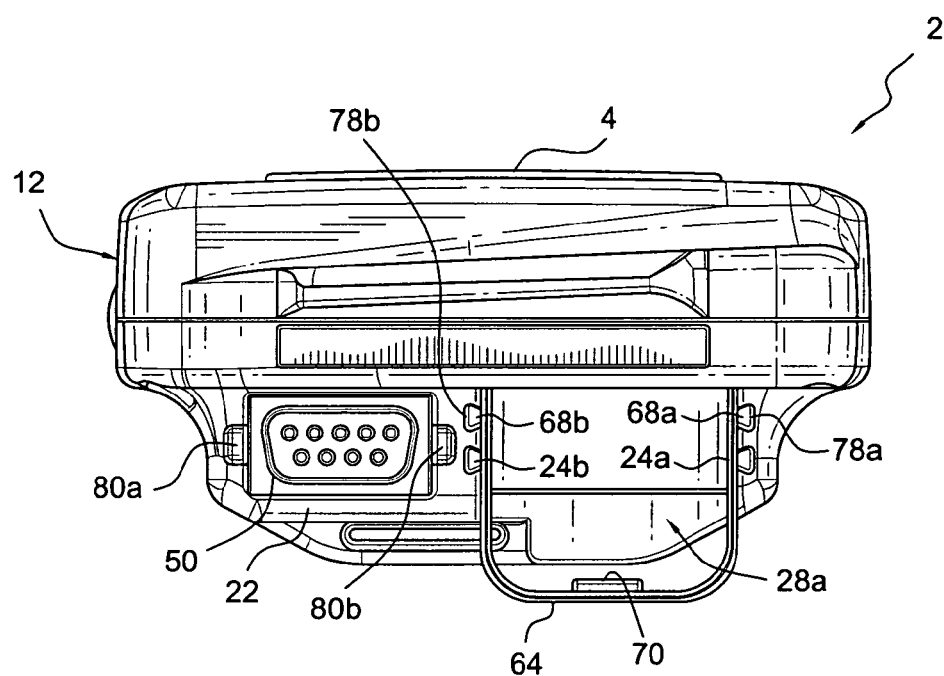
FIG. 13 is a top view of the oximeter device of the instant invention showing a connector in a compartment and the attachment of a receptacle cover to the oximeter housing for establishing a receptacle.

To effect the pocket receptacle or holster into which sensor 52 is to be retained, receptacle cover 60 is slidingly fitted into the portion of housing 12 that defines cavity 28, by fittingly sliding its edge guides 68a and 68b with the respective grooves 78a and 78b formed along the corresponding sidewalls 24a and 24b that extend from back wall 18 of cavity 28. Once fully inserted into to the housing 12, receptacle cover 60 along with the back wall 18 of cavity 28 form the receptacle for retaining the corresponding sensor, for example sensor 52 shown in FIG. 9. The thus configured receptacle 28a is best shown in FIG. 13. As should be apparent, the dimension for receptacle 28a would vary, depending on which of the plurality of sensors shown in FIGS. 5-8 is to be used with oximeter 2 and which of the plurality of receptacle covers 60a, 60b or 60c is to be fitted to housing 12 for effecting the receptacle, pocket or holster needed to retain the to be used sensor.

As receptacle cover 60 is attached to the cavity defining portion of housing 12, the edge 66a (FIG. 10a) of the end insert 66 of the cover would come into contact with protuberance 30. Upon contact, due to the inherent elastic property of the plastics material from which the cover is made, the end insert would flex over the protuberance and be latched thereby. End insert 66 then form fittingly seats onto base 26 of cavity 28. Receptacle cover 60 can be removed from cavity 28 by a user asserting a predetermined force to overcome the latching of the cover 60 by protuberance 30. Depending on the type of sensor, and the sensor assembly associate therewith, to be used with oximeter 2, different ones of the receptacle covers 60 may be affixed to housing 12 of oximeter 2.

Figure 17:
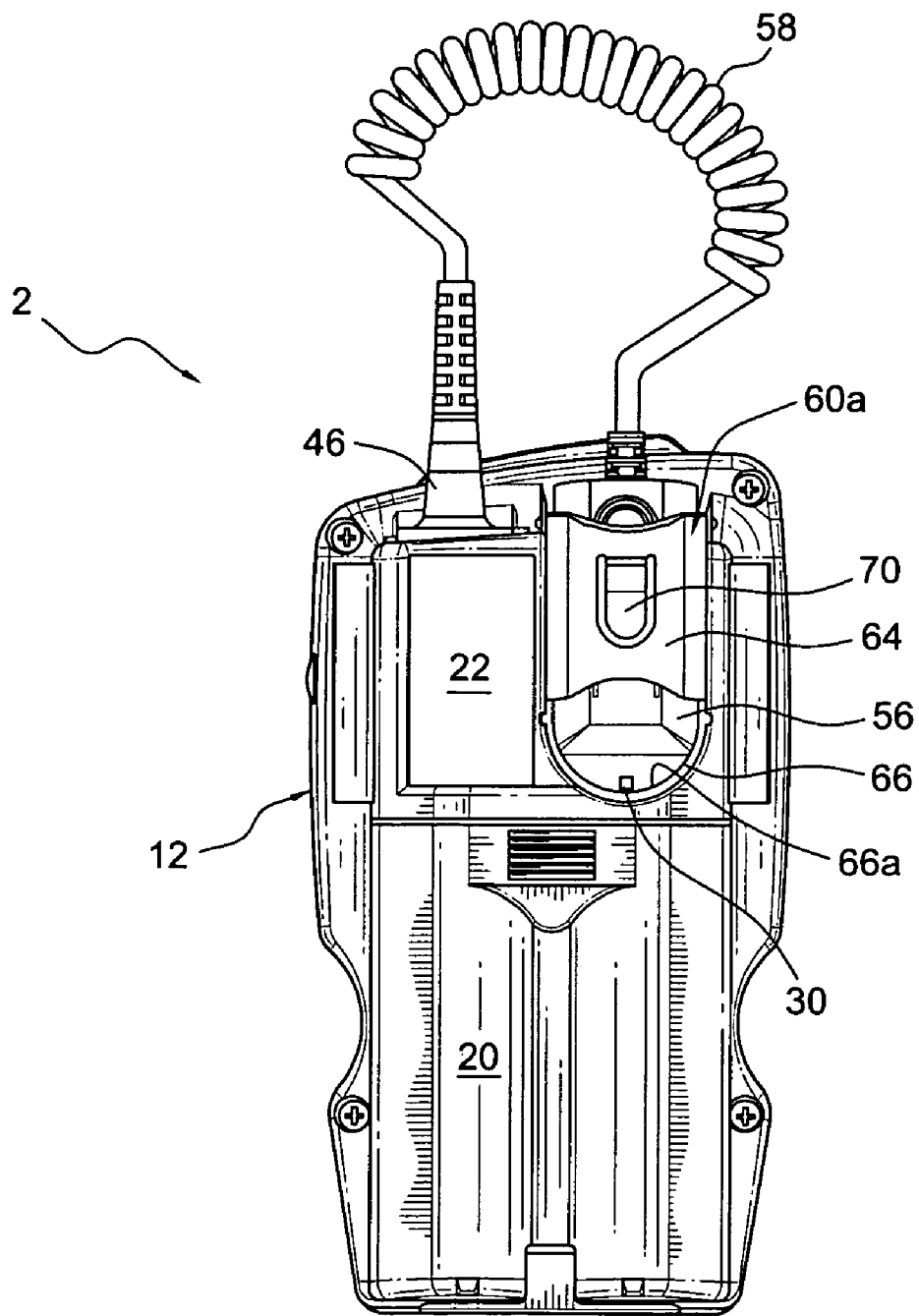
FIG. 17 shows a back view of the oximeter device with a receptacle, and a coiled cable sensor assembly having its sensor holstered in the receptacle and its connector coupled to the oximeter.

After a given receptacle cover 60 is affixed to housing 12 to form receptacle 28a, the corresponding sensor can be placed into and stored in receptacle 28a when it is not in use. Tongue 70 at the front wall 64 of the receptacle cover 60 biases against the surface of the sensor that it makes contact with so that the senor is pushed against back wall 18 of housing 12. As a result, once placed into receptacle 28a, the sensor is firmly held therein unless the user deliberately exerts a force that is greater than the biasing force exerted by tongue 70 against the sensor to remove the sensor from the receptacle 28a. FIG. 17 is an illustration showing the storage of a sensor in the receptacle that is formed by the affixing of a receptacle cover to the housing of the oximeter.

With reference to FIG. 13, at the interior of compartment 22 at the back of oximeter housing 12 is connector 50 for coupling with sensor connector 46 of the sensor assemblies of FIGS. 5-8. Connector 46 is guided into the interior of compartment 22 by its ears 46c and 46d fittingly slide along two corresponding slots 80a and 80b formed at the interior of compartment 23.

Figure 14:
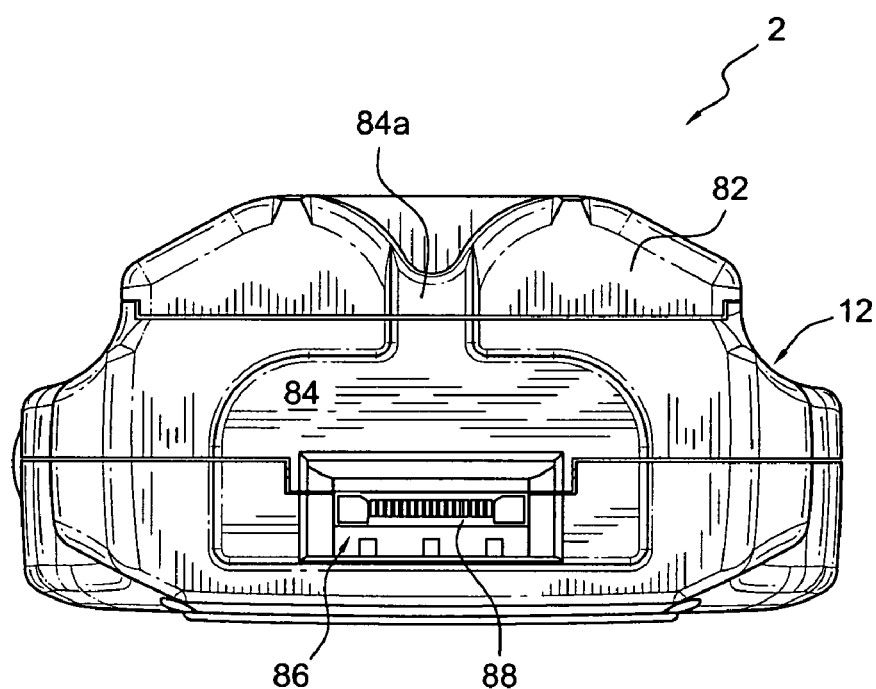
FIG. 14 is a bottom view of the oximeter device of the instant invention and a connector internal thereto.

With reference to FIG. 14, a bottom view shows that the bottom surface 82 of the oximeter device 2 has an opening 84 with a passage 84a toward the back of housing 12. Opening 84 leads to a chamber 86 whereto there is mounted a connector, for example a USB connector, that is adapted to be mated to a counterpart connector. The connector can be connector 90 in a docking station (FIG. 21), or a conventional USB cable conencter for supplying power and/or establishing communication between the oximeter device 2 and an external device. If connector 80 were to couple to a USB cable, the body of the cable can pass through passage 84a, so that housing 12 can stand upright on a flat surface.

Figure 15:
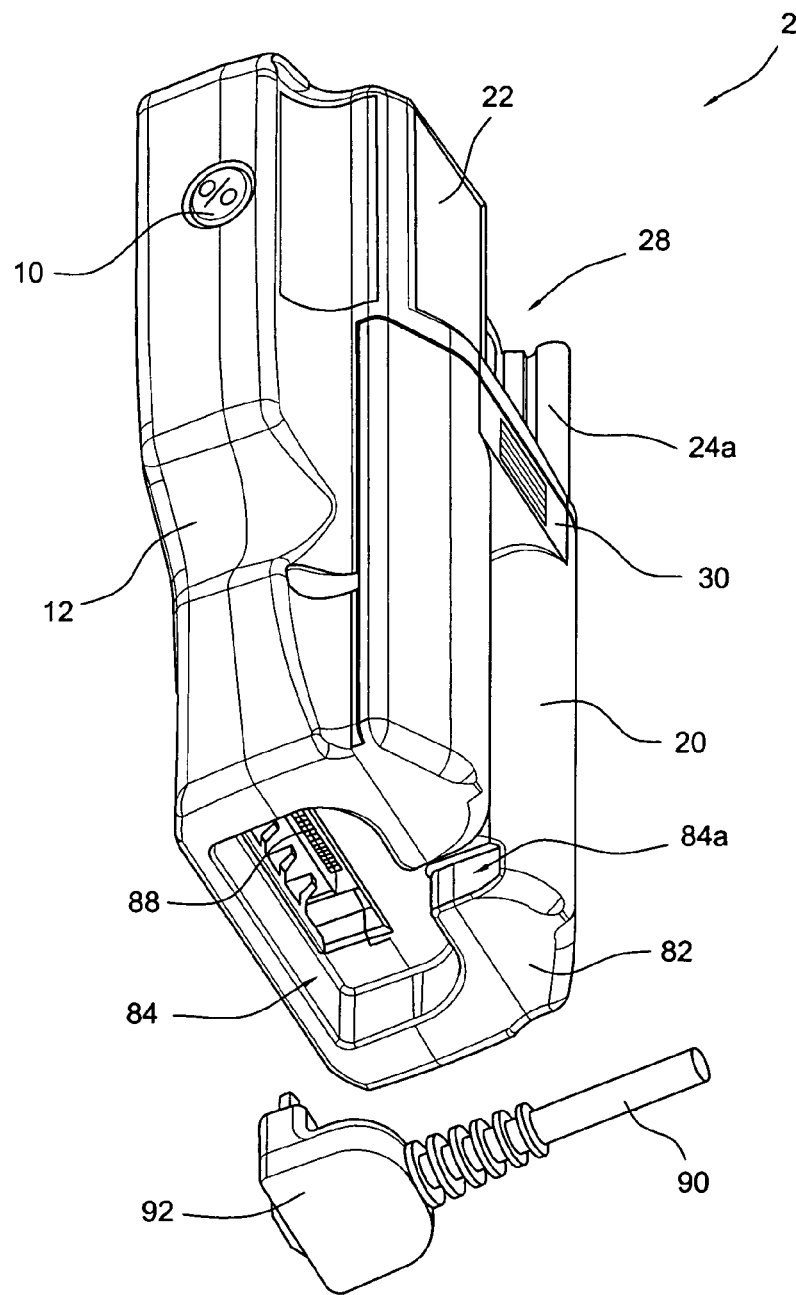
FIG. 15 is a perspective view showing the bottom of the oximeter device, its internal connector and a connector of a connector assembly that is to be coupled to the internal connector.

FIG. 15 shows a USB cable assembly with its connector 92 configured to mate to connector 88 in chamber 86 of oximeter housing 12. Cable 90 fits into passage 84a while the body of connector 92 fits into opening 84, to thereby enable oximeter 2 to stand upright on a flat surface. With the connection of cable 90 to oximeter 2, as was noted earlier, a communication path is established between oximeter 2 and another device, for example an external monitor or another oximeter that has the capability to monitor remotely the physical attributes being monitored by oximeter 2, via the sensor of the sensor assemblies shown in FIGS. 5-8 connected thereto. The ability of oximeter 2 to communicate with another device is disclosed in the aforenoted incorporated by reference co-pending applications. With the connection of cable 90 to oximeter 2, in addition to establishing an electrical communications path, external power may also be supplied to oximeter 2.

Figure 16:
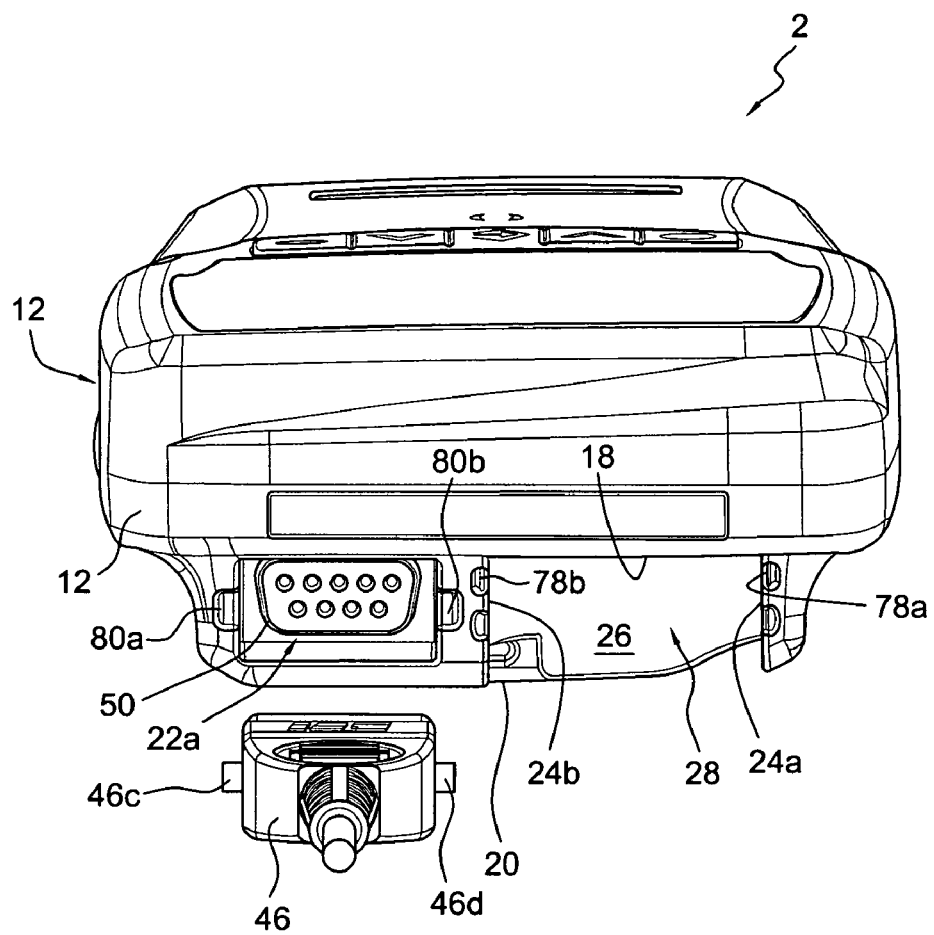
FIG. 16 is an illustration of the top of the oximeter device, its upper connector and its relationship to a connector of a sensor assembly that is to be connected thereto.

FIG. 16 shows the relationship between any one of the sensor assemblies of FIGS. 5-8 and oximeter 2. As shown, connector 46 of a cable of one of the sensor assemblies as noted is matable to connector 50, for example a DB-9 connecter mounted in chamber 22a of compartment 22. Slots 80a and 80b provide guidance for ears 46c and 46d of connector 46, so that connector 46 would be securely guided to and mate with connector 50. Physical attributes measured by the sensor of the sensor assembly are routed to oximeter 2 so that the measured physical attributed may be displayed on screen 4 of the oximeter, as is well known and performed by the oximeter boards discussed earlier.

FIG. 17 shows the connection of a coiled sensor assembly such as that shown in FIG. 8 to oximeter 2, with connector 46 of the sensor assembly mated to connector 50 in compartment 22 of oximeter housing 12. FIG. 17 also shows sensor 56 being retained within the receptacle or holster effected by the affixing of receptacle or clip cover 60, in this instance 60a of FIGS. 10a-10g, to housing 12. FIG. 17 further shows the coaction between edge 66a of the end insert 66 of cover 60a with the protuberance 30 at back wall 18 of housing 12, for affixing cover 60a to housing 12. Absent a predetermined force large enough to dislodge cover 60a from the latching effected by protuberance 30, cover 60a stays firmly affixed to housing 12. Moreover, sensor 56 is frictionally retained in receptacle 28a due to it being biased by tongue 70 against back wall 18 of the receptacle.

Figure 18:
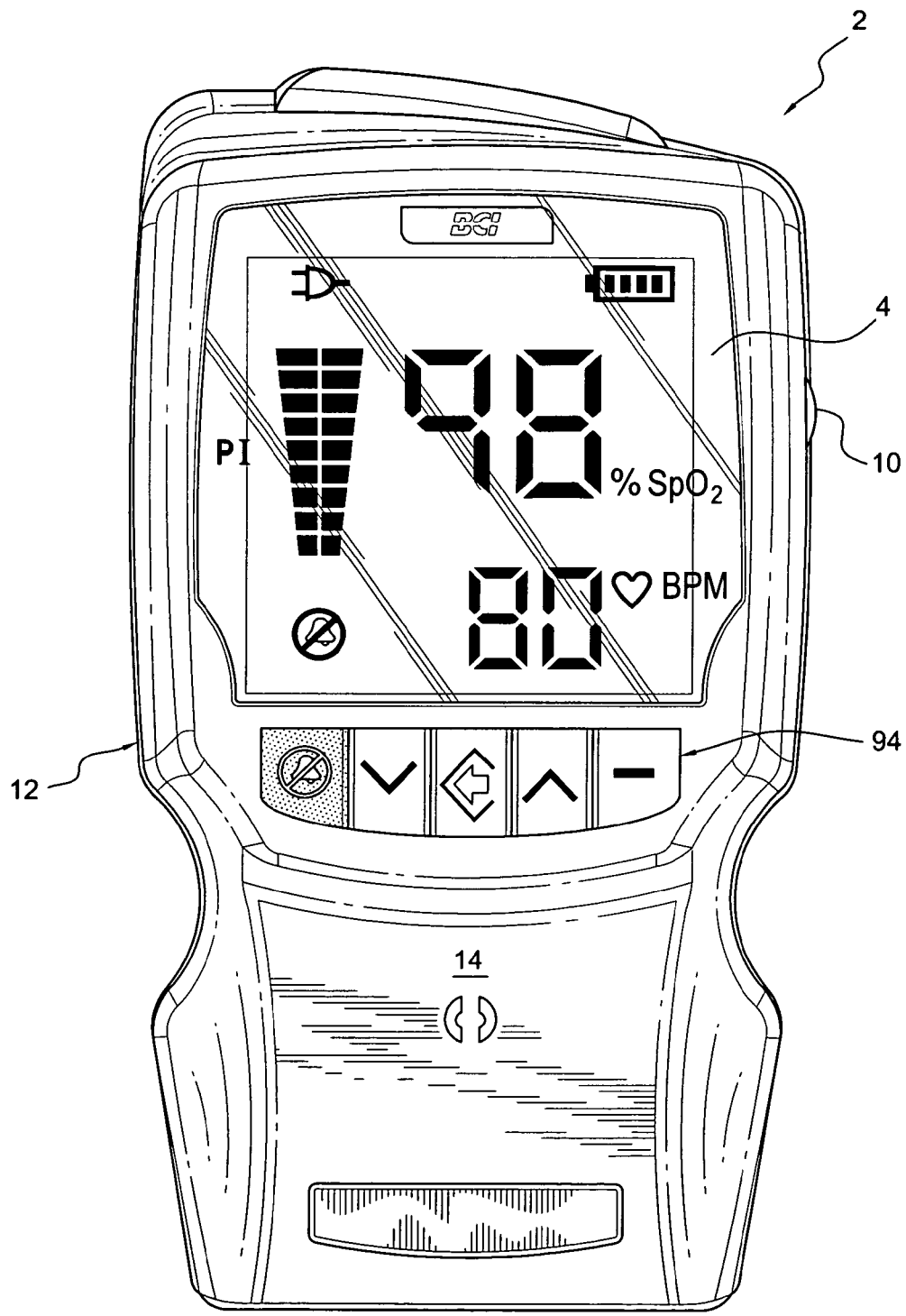
FIG. 18 is a front view of another embodiment of the oximeter device of the present invention.

FIG. 18 is a front view of a second embodiment of the oximeter of the instant invention in which a number of button switches 94 have been added to the front surface of housing 12. These buttons provide the user additional capabilities, such as changing screen 4 to display other numerical or graphical representations, or other functions that are described in the aforenoted incorporated by reference co-pending applications.

Figure 19:
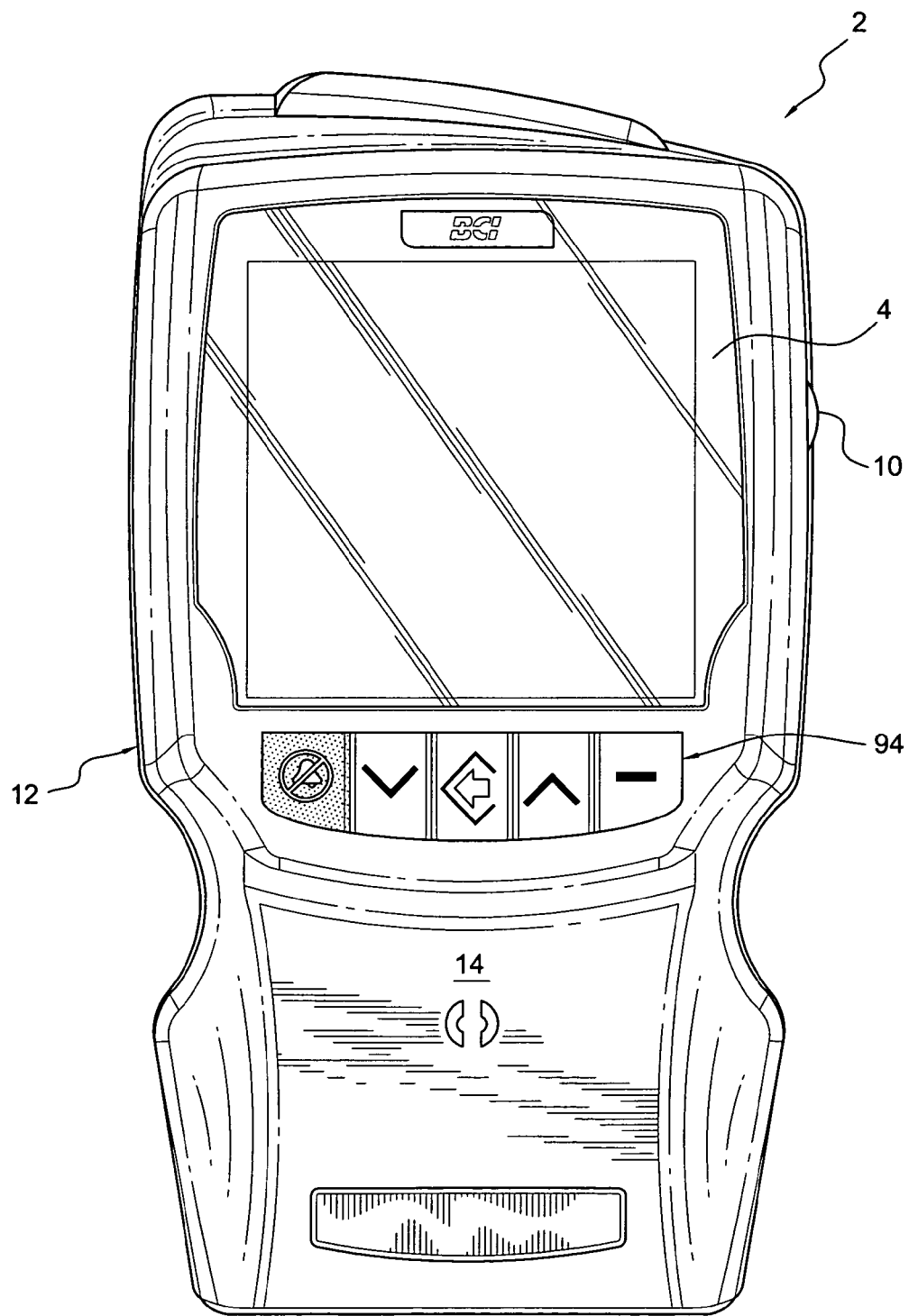
FIG. 19 is the front view of yet another embodiment of the oximeter device of the present invention.

FIG. 19 shows another embodiment of the oximeter 2 of the instant invention in which screen 4 is a LCD screen to enable the display of additional graphics and numbers that may represent sensed physical attributes of a patient or additional information for the user of the oximeter, such as text messages including instructions, conditions of the patient and alarms. Oximeter 2 of the FIG. 19 embodiment further provides the user a way of communicating with other devices including other oximeters that may communicate telecommunicationally without the need for cables as described in the aforenoted incorporated by reference co-applications.

Figure 20:
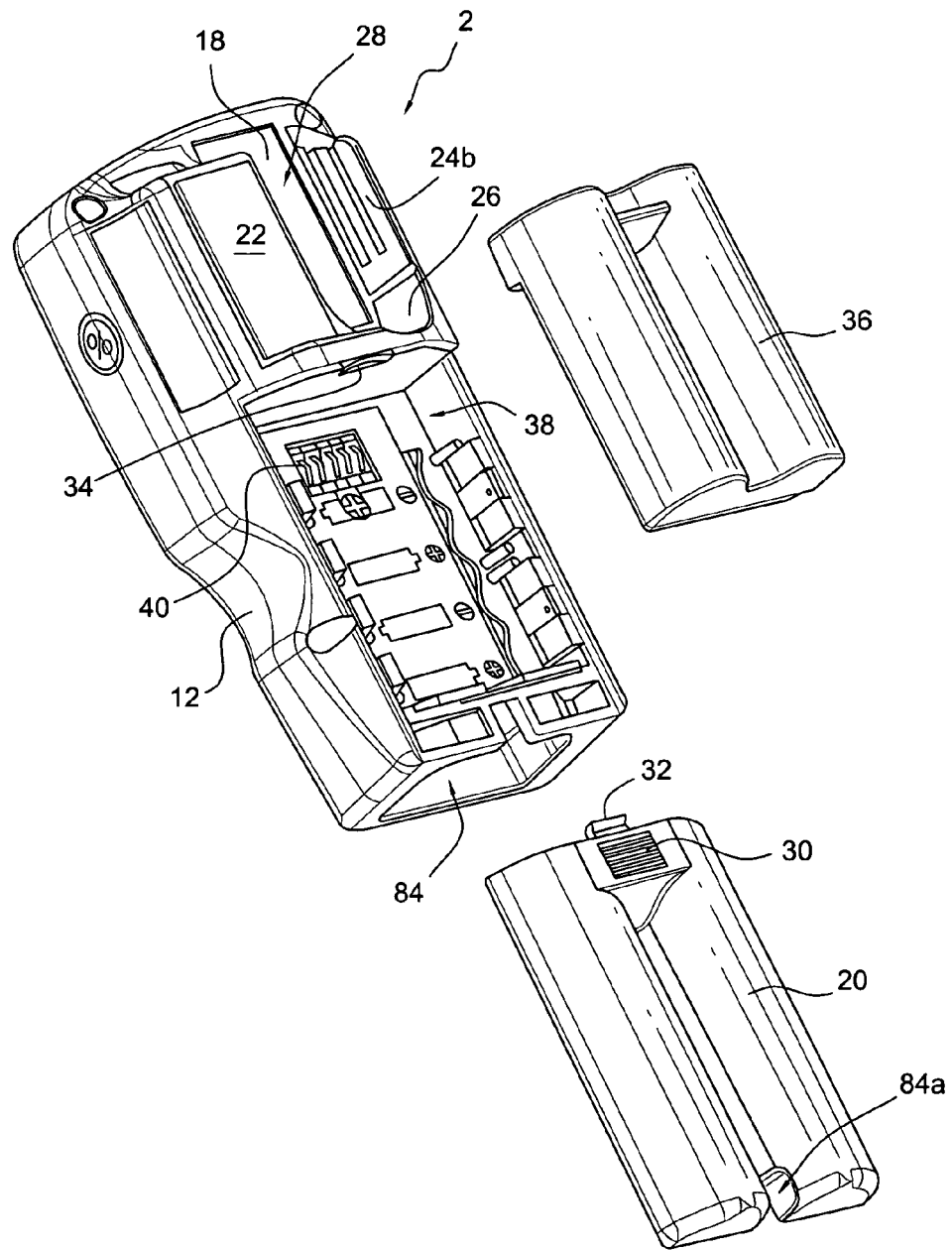
FIG. 20 is a disassembled perspective view of the back of the oximeter device of the present invention.

FIG. 20 shows a perspective back view of oximeter 2 in which a battery pack 36 has been removed from chamber 38 and cover 20 has been removed from housing 12. Cover 20 is configured to have a part of passage 84a at its lower portion formed.

Figure 21:
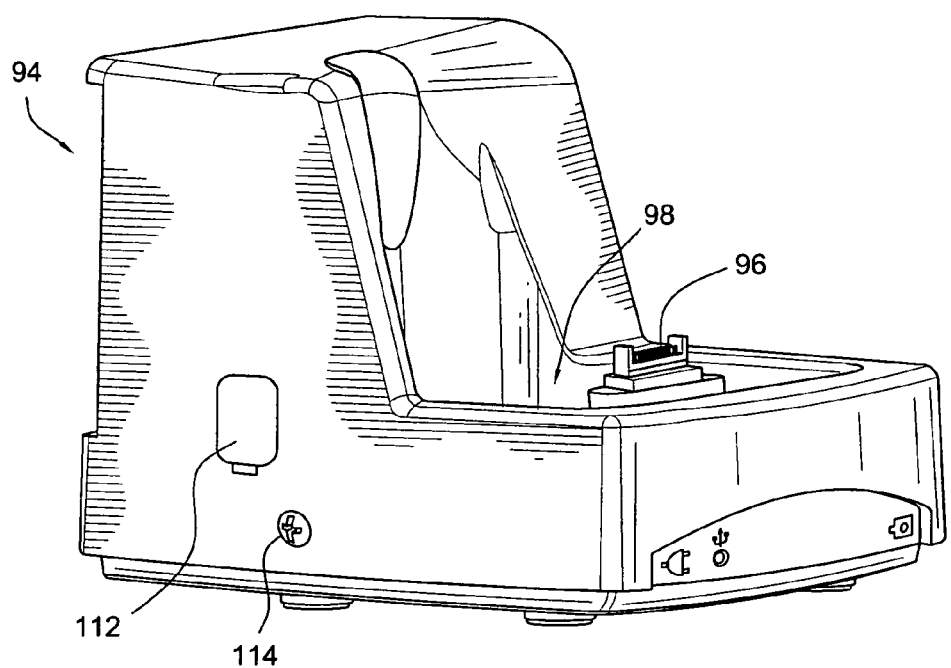
FIG. 21 is a perspective view of a docking station to be used with the oximeter device of the instant invention.

FIG. 21 is a perspective view of a docking station 94 to which oximeter 2 may dock. To dock, the USB connector 88 (FIG. 15) of oximeter 2 is mated to a counterpart connector 96 at docking station 94. Connector 96 may be a Molex connector that can deliver power to oximeter 2 and establish a communication path between docking station 94 and oximeter 2. A cradle area 98 is provided in docking station 94 to enable housing 12 of the oximeter to be securely positioned, when oximeter 2 is docked to docking station 94. The docking of oximeter 2 to docking station 94 is best shown in FIG. 23.

Figure 22B:
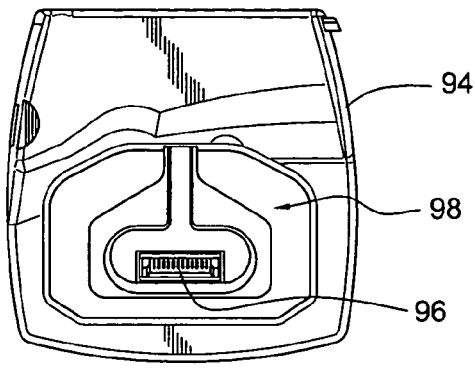
FIGS. 22a, 22b, 22c, 22d and 22e are respective views of the front, the top, the bottom, the side and the back of the docking station of FIG. 21.
Figure 22A:
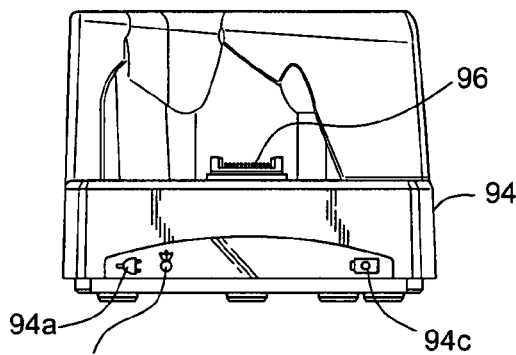

FIGS. 22a-22e are different illustrations of the docking station. FIG. 22a shows the front of the docking station in which a number of informational lights are provided. For example, when the oximeter is docked to docking station 94, a lit LED at 94a shows that AC power is being provided to the docking station, and a lit LED at 94b shows USB power is available and is being provided to the oximeter. A spare battery charging light, designated by 94c, shows that a spare battery 100 (FIG. 23) in docking station 94 is being charged. Battery pack 100 is inserted into a chamber (not shown) behind door 102 at the back of docking station 94, per shown in FIG. 22e. The door is shown to be opened in FIG. 23.

Figure 22D:
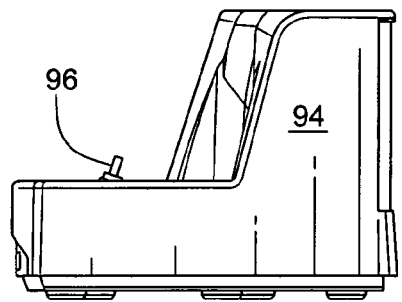
Figure 22C:
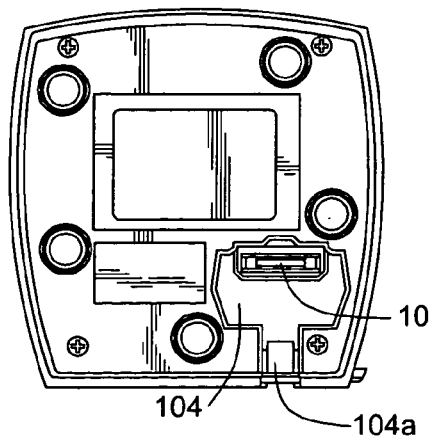
Figure 22E:
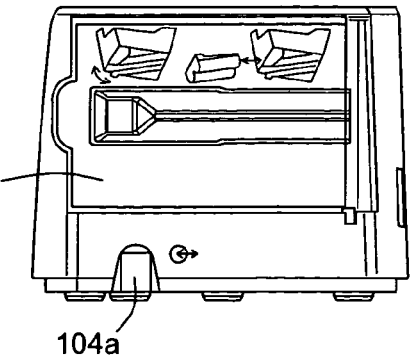

FIG. 22b shows a plan view of the top of docking station 94, showing the chamber 98 whereto the oximeter is positioned and cradled, and connector 96 to which the USB connector 88 of oximeter 2 is coupled. FIG. 22d shows a side view of the docking station 94. FIG. 22c shows the bottom view of docking station 94. As shown, a connector 106 is provided inside a chamber 104 having a side passageway. Connector 106 enables docking station 94 to be connected to an external device or a power device, so that a communications path and/or a power path may be established between the external device and the oximeter docked to the docking station. The cable assembly to be used with docking station 94 may be same as the cable assembly 90 shown in FIG. 15. In FIG. 22e, graphical representations informing a user of how to insert and remove a battery pack are printed on backdoor 102.

Figure 23:
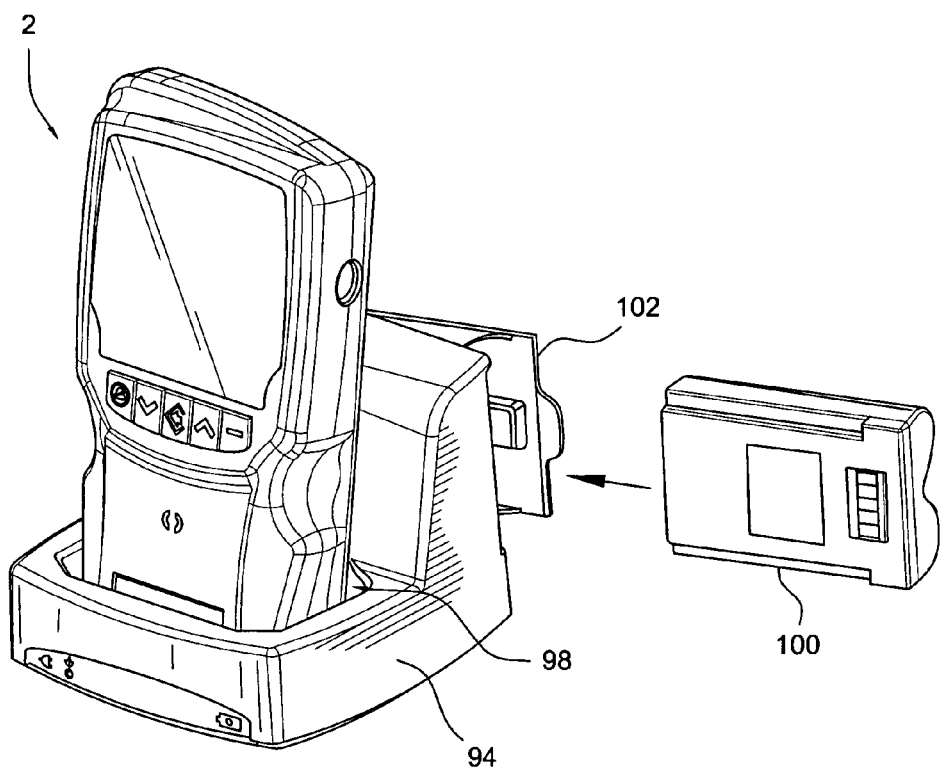
FIG. 23 is a perspective view showing the docking of the oximeter device to the docking station and the battery pack of the docking station removed from the docking station.

FIG. 23 shows the docking of oximeter 2 to the docking station 94, the opening of door 102 at the back of docking station 94, and the battery pack 100 having been removed from docking station 94.

FIGS. 24a-24e are different views of a printer 108 that is attachable to docking station 94 to enable information from the oximeter to be printed. Printer 24a has a side 108a that includes a door 110 that may be pivotally open, per shown in FIG. 27, to allow a roll of printing paper to be installed into printer 108. Printer 108 has a top that contains various switches and designations for a user, per shown by top view 108b of FIG. 24c. A side surface 108c shows how a roll of paper may be inputted to the printer and how door 110 is to be opened and closed. An inside surface view of printer 108 in FIG. 24b shows a connector 110 that mates with a corresponding connector (not shown as it is behind cover 112 of docking station 94 in FIG. 21) at docking station 94. Connector 110, when connected to the connector behind cover 112 of docking station 94, provides communication between docking station 94 and printer 108. The alignment of printer 108 to dock 94 is effected by removing screw 114 at the side of the docking station 94 and the insertion thereto by guiding post 116 at the side surface 108d of printer 108, per shown in FIG. 24b.

Figure 25:
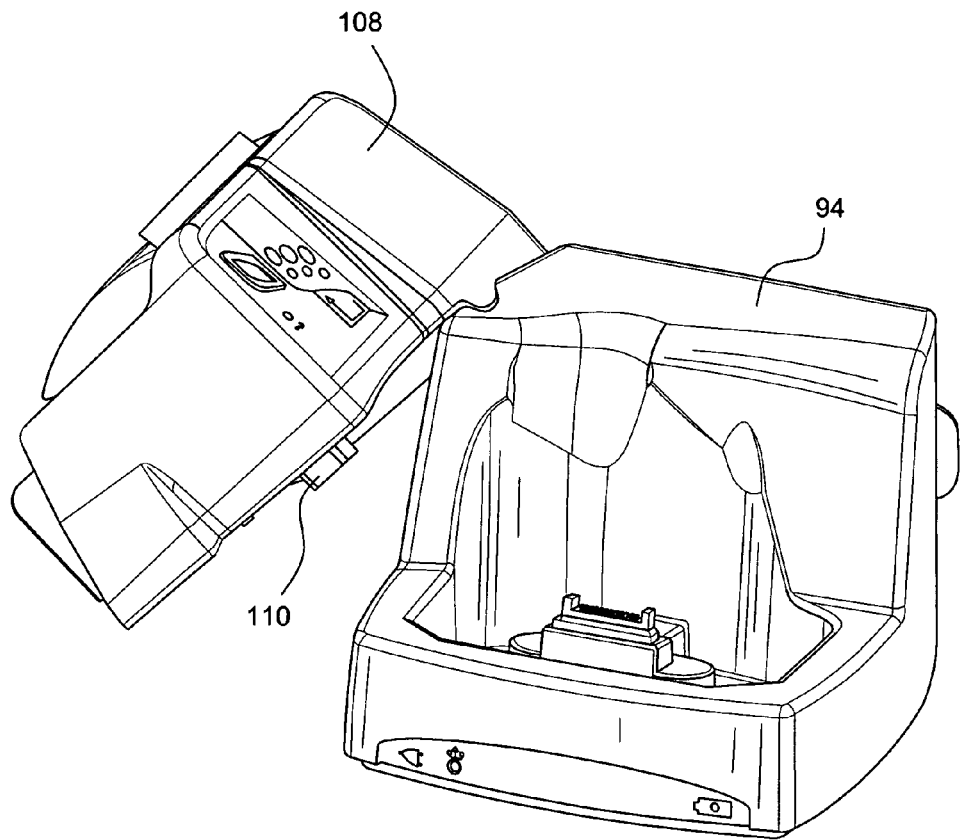
FIG. 25 is an illustration of a partial coupling of the printer to the docking station.
Figure 26:
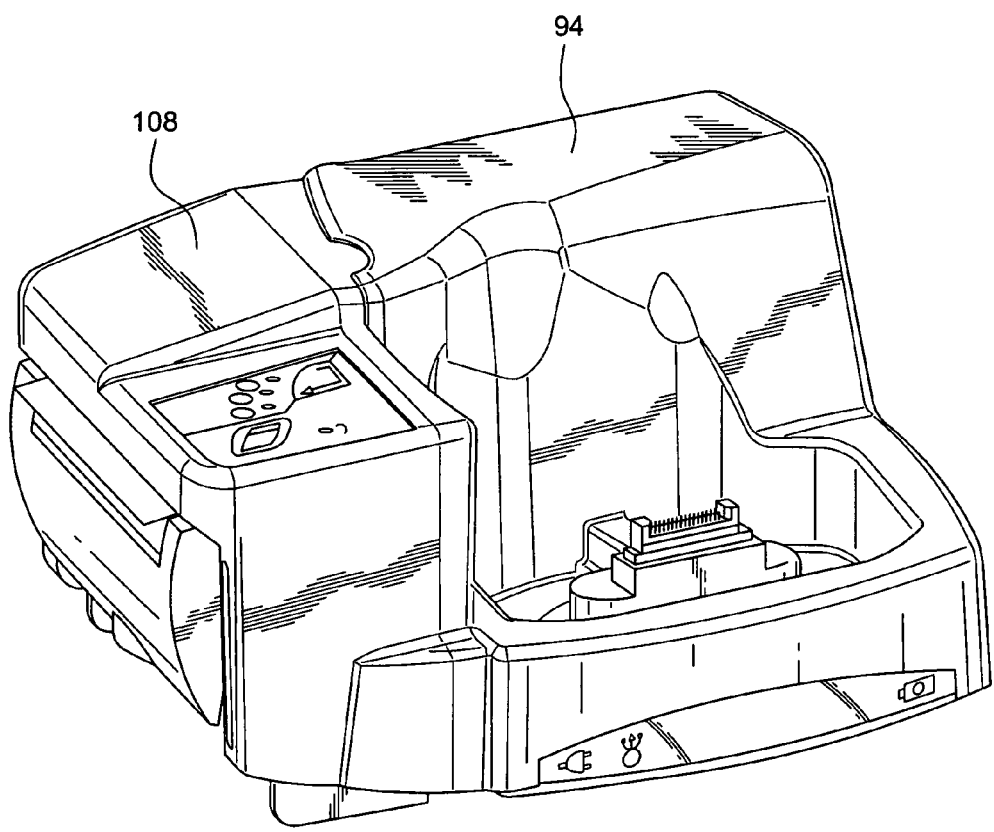
FIG. 26 shows a system that has the printer coupled to the docking station.

FIG. 25 shows printer 108 being hingedly attached to docking station 94, and FIG. 26 shows the coupling of printing station 108 to docking station 84. The system formed by the combined docking station 94 and printer 108 allows a user, once oximeter 2 is cradled in docking station 94, to print out information from the oximeter and docking station, and the transmitting of information between oximeter 2 and the docking station 94 as well as to a remote device, if docking station 94 were to be electrically connected by means of its connector its 106 (FIG. 22c) to the remote device.

Figure 27:
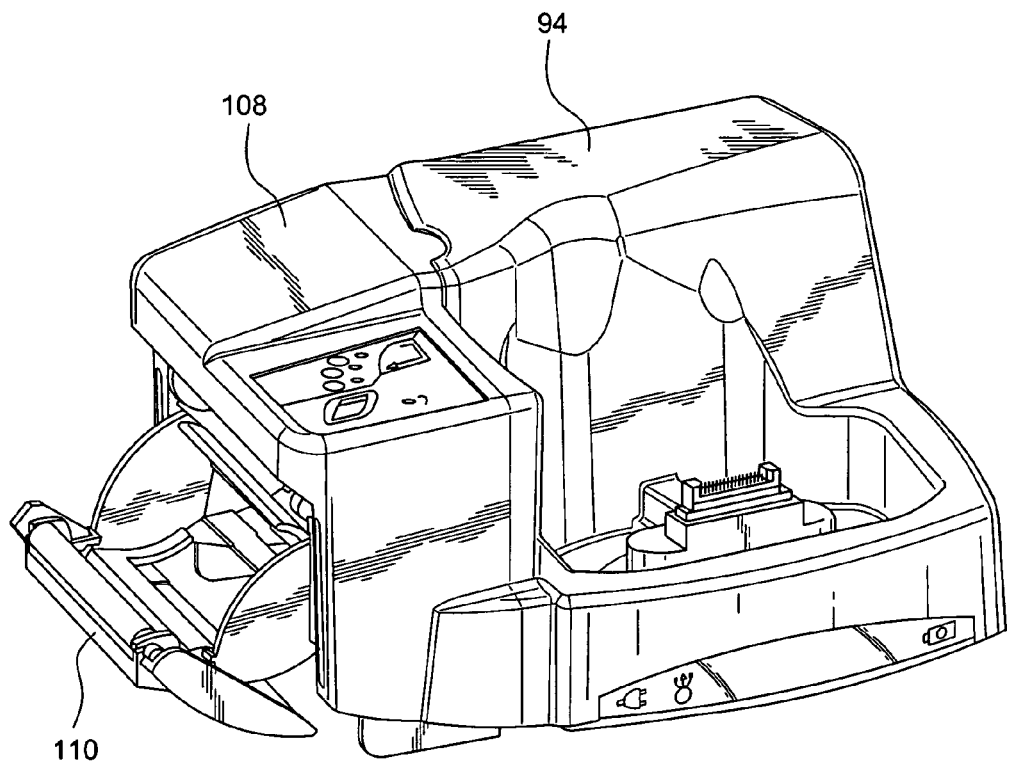
FIG. 27 shows the paper container of the printer opened and in position for receiving a new roll of paper.

FIG. 27 shows the system of a, combination of printer 108 and docking station 94 with door 110 opened, possibly to receive a new roll of paper.

Inasmuch as the present invention is subject to many variations, modifications and changes in detail, it is intended that all matter throughout this specification and shown in the accompanying drawings be interpreted as illustrative only and not in a limiting sense. Accordingly, it is intended that the invention be limited only by the spirit and scope of the appended claims. For example, even though an oximeter is described hereinabove, it should be appreciated that a medical device that uses sensors for measuring physical attributes or physiological parameters of a patient may also use the instant invention in that the housing of the medical device may be configured to accept covers or clips of different dimensions so that sensors of different dimensions can be accommodated and carried with the medical device.

The invention claimed is:

1. Apparatus comprising: a housing having a front and back, a screen at the front for displaying graphical or numerical representations of sensed physical attributes of a patient, said housing having one connector adapted to mate with a sensor connector of a sensor assembly, the sensor connector electrically connected to a sensor of the sensor assembly which is attachable to the patient to sense at least one physical attribute of the patient, said housing further having a cavity defined by a cavity portion at the back of said housing configured to accept any one of a plurality of covers of different dimensions adapted to retain a corresponding plurality of sensors of different dimensions, said any one cover is removably affixed to said cavity portion until a predetermined force is applied to remove it from said cavity portion, said any one cover dimensioned to fittingly accept only a corresponding sensor of a given dimension from the plurality of sensors of different dimensions that once placed in said receptacle is securely held therein unless deliberately removed therefrom.

2. Apparatus of claim 1, wherein said any one cover comprises a tongue that biases against one surface of the corresponding sensor after the corresponding sensor is inserted in said receptacle to cause the corresponding sensor to be frictionally retained in said receptacle absent a deliberate movement to remove it from said receptacle.

3. Apparatus of claim 1, wherein said cavity is defined by said cavity portion comprising an exterior back wall, a base and two sidewalls each extending from the back of said housing, a protuberance formed at the back wall adjacent to the base; and wherein said any one cover has an end insert that coacts with the protuberance to prevent said any one cover from being removed from said cavity portion absent the predetermined force being applied to remove it from said cavity portion.

4. Apparatus of claim 1, wherein each of said covers is configured in the shape of a holster with two sidewalls extending from a front wall that includes a tongue, the two sidewalls connected by a curved base that extends downwardly beyond the front wall, a flange formed at the edge of each of the sidewalls away from the front wall to guide the insertion of said each cover into said cavity portion, the curved base form fits to a curved base at said cavity portion once said each cover is fully inserted into said cavity portion.

5. Apparatus of claim 4, wherein each of said covers does not have a back wall and wherein the respective flanges at the sidewalls of said each cover fittingly slide along corresponding grooves at the sidewalls of said cavity portion for guiding the insertion of said each cover into said cavity portion.

6. Apparatus of claim 3, wherein the base of said cavity portion has a curved configuration; and wherein the end insert of each of said covers comprises a curved band that form fits to the curved base when said each cover is inserted into said cavity portion, one edge of the curved band coacting with the protuberance to non-fixedly affix said each cover to said cavity portion.

7. Apparatus of claim 1, wherein respective ones of said covers when affixed to said cavity portion form corresponding receptacles of different dimensions, a first receptacle having a first dimension adapted to hold a finger sensor with a head portion pivotable relative to a base portion, a second of said receptacles having a second dimension adapted to hold a sensor having two head portions pivotable relative to each other, and a third of said receptacles having a third dimension adapted to hold a pediatric sensor.

8. Apparatus of claim 7, wherein each of the first, second and third sensors comprises a cable connecting the respective sensors to corresponding sensor connectors, each of the sensor connectors matable with said one connector at said housing; and wherein selective ones of the sensor connectors comprise a grab tab formed at right angle to the sensor connector to facilitate the mating and removal of the sensor connecter to and from said one connector.

9. Apparatus of claim 1, further comprising a sensor assembly having a sensor connected by a coiled cable to a sensor connector mated to said one connector, said sensor having a sensor head postionable in a counterpart receptacle formed by a given cover removably affixed to said cavity portion.

10. Apparatus of claim 1, wherein said housing further comprises an other connector connectable to a power or USB connector for receiving power and/or effecting communication between said apparatus and another device.

11. Apparatus of claim 10, wherein said apparatus comprises an oximeter matable to a docking station, said docking station having a cradle area whereonto said oximeter is positioned, said other connector from said housing mating to a dock connector to enable operation of said oximeter and/or recharging of a power source of said oximeter.

12. Apparatus of claim 11, wherein said docking station is configured electrically and mechanically to have coupled thereto a printer adapted to at least print out data from said oximeter.

13. An oximeter comprising a housing having a screen mounted to its front for displaying at least one graphical or numerical representation of at least one physical attribute of a patient, one connector adapted to mate with a sensor connector of a sensor assembly, the sensor connector electrically connected to a sensor of the sensor assembly which is attachable to the patient to sense the physical attribute of the patient, a cavity defined by a cavity portion at the back of said housing configured to accept any one of a plurality of covers of different dimensions adapted to retain a corresponding plurality of sensors of different dimensions, said any one cover once inserted into said cavity portion is affixed thereto until a predetermined force is applied to remove it from said cavity portion, said any one cover when affixed to said cavity portion form a receptacle dimensioned to fittingly accept only a corresponding one sensor of a given dimension from the plurality of sensors of different dimensions, said one sensor being securely held in but readily removable from said receptacle once it is placed in said receptacle, and a chamber at the back of said housing for storing power source.

14. Device of claim 13, wherein said any one cover comprises a tongue that biases said one sensor against a surface at the back of said housing after said one sensor is placed to said receptacle so that said one sensor is retained in said receptacle absent a deliberate attempt by a user to remove it from said receptacle.

15. Device of claim 13, wherein said cavity portion is defined by an exterior wall at the back of said housing, two sidewalls each extending from the exterior wall and coming together to form a curved base, a protuberance formed at the exterior wall proximate to the curved base; and wherein said any one cover has a curved end insert that form fits to the curved base and coacts with the protuberance to prevent said any one cover from being removed from said cavity portion absent the predetermined force being applied to remove it from said cavity portion.

16. Device of claim 14, wherein each of said covers comprises respective guides at its sides adapted to fittingly slide along corresponding grooves at the sidewalls of said cavity portion for guiding the insertion of said each cover into said cavity portion.

17. Device of claim 14, wherein said housing comprises an other connector inwardly provided at its base connectable to a power or universal serial bus (USB) connector for receiving power and/or effecting communication between said oximeter device and another device.

18. A system, comprising:
an oximeter having a screen mounted to its front for displaying graphical or numerical representations of physical attributes from a patient, one connector adapted to mate with a sensor connector of a sensor assembly, the sensor connector electrically connected to a sensor of the sensor assembly which is attachable to the patient to sense at least one physical attribute of the patient, a cavity portion configured to accept any one of a plurality of covers of different dimensions adapted to retain a corresponding plurality of sensors of different dimensions, said any one cover once inserted into said cavity portion is affixed thereto until a predetermined force is applied to remove it from said cavity portion, said cavity portion and said any one cover affixed thereto together form a receptacle dimensioned to fittingly accept only a corresponding one sensor of a given dimension from the plurality of sensors of different dimensions so that the corresponding one sensor is securely held in but removable from said receptacle, and an other connector; and
a docking station whereonto said oximeter is docked, said other connector from said oximeter matable to a dock connector when said oximeter device is docked to said docking station.

19. System of claim 18, further comprising a printer connectable to said docking station for printing out data from said oximeter device.

20. System of claim 18, wherein said oximeter comprises a power source that enables said oximeter to be operable when it is not docked to said docking station, the power source rechargeable when said oximeter is docked to said docking station or when said other connector is connected to a power or a universal serial bus (USB) cable, a communication path established to said oximeter from said docking station or the USB cable when said oximeter is docked to said docking station or connected to the USB cable.

* * * * *